US012778588B2

(12) United States Patent
Sejor et al.

(10) Patent No.: US 12,778,588 B2
(45) Date of Patent: Nov. 3, 2026

(54) APPARATUS AND METHOD FOR ENDOSCOPIC ANASTOMOSIS OF THE STOMACH AND THE BOWEL

(71) Applicant: BariaTek Medical, Paris (FR)

(72) Inventors: Eric Sejor, Nice (FR); Youssef Biadillah, Maisons-Laffitte (FR)

(73) Assignee: BariaTek Medical, Paris (FR)

( * ) Notice: Subject to any disclaimer, the term of this patent is extended or adjusted under 35 U.S.C. 154(b) by 370 days.

(21) Appl. No.: 18/552,258

(22) PCT Filed: Mar. 25, 2022

(86) PCT No.: PCT/EP2022/057913
§ 371 (c)(1),
(2) Date: Sep. 25, 2023

(87) PCT Pub. No.: WO2022/200566
PCT Pub. Date: Sep. 29, 2022

(65) Prior Publication Data

US 2024/0197322 A1 Jun. 20, 2024

(30) Foreign Application Priority Data

Mar. 26, 2021 (EP) .................................... 21165399

(51) Int. Cl.
*A61B 17/11* (2006.01)
*A61B 17/00* (2006.01)
(Continued)

(52) U.S. Cl.
CPC ...... *A61B 17/1114* (2013.01); *A61B 17/0469* (2013.01); *A61B 17/115* (2013.01);
(Continued)

(58) Field of Classification Search
None
See application file for complete search history.

(56) References Cited

U.S. PATENT DOCUMENTS

2002/0077637 A1* 6/2002 Vargas ............... A61B 17/3468 606/153
2003/0120292 A1* 6/2003 Park ..................... A61B 17/083 606/153
(Continued)

FOREIGN PATENT DOCUMENTS

EP 3 005 993 A2 4/2016
WO 2011/149876 A2 12/2011

OTHER PUBLICATIONS

European Search Report Corresponding to 21165399.3 mailed Sep. 16, 2021.
(Continued)

*Primary Examiner* — Shaun L David
(74) *Attorney, Agent, or Firm* — Secant IP, P.L.L.C.

(57) ABSTRACT

Apparatus for endoscopic anastomosis of the stomach and the bowel of a patient to allow food to bypass the duodenum and optionally a portion of the jejunum comprising a tube, surgical apparatus and at least one operating element. The tube is insertable into the stomach and has a proximal end and a distal end. The surgical apparatus is at least partially, preferably completely, insertable through the tube. The operating element, for operating the surgical apparatus from the proximal end, is connected or connectable to the surgical apparatus. The surgical apparatus is configured for establishing anastomosis between a first area of the stomach and a second area of the bowel.

24 Claims, 17 Drawing Sheets

Figure 1:
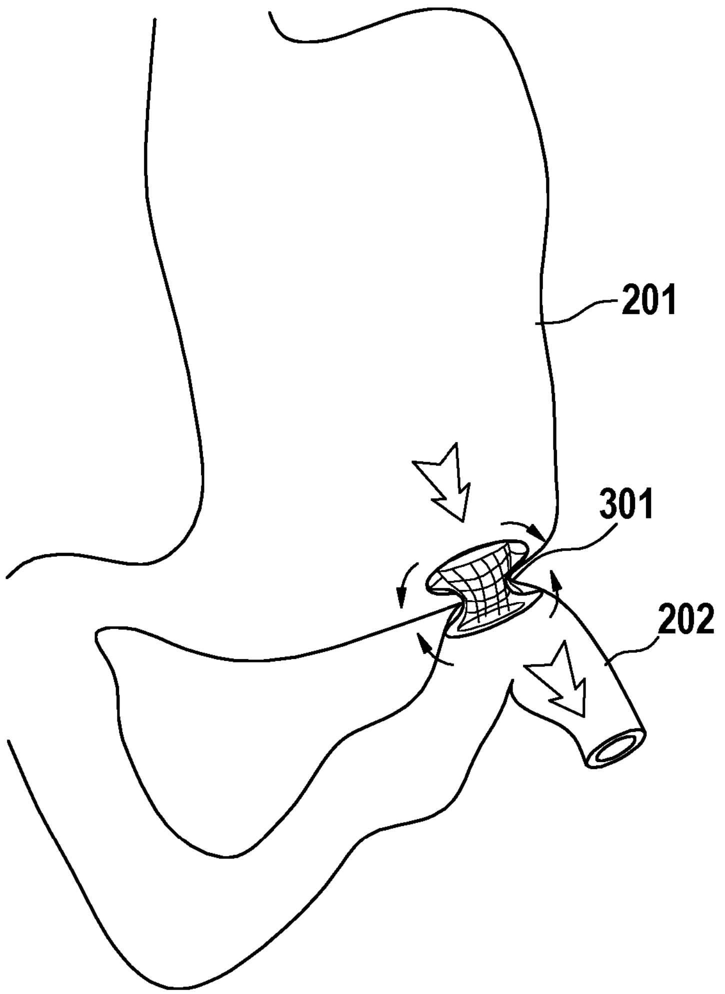

(51) Int. Cl.
*A61B 17/04* (2006.01)
*A61B 17/115* (2006.01)
*A61B 17/32* (2006.01)
*A61B 90/00* (2016.01)

(52) U.S. Cl.
CPC ........ *A61B 17/32002* (2013.01); *A61B 90/08* (2016.02); *A61B 2017/00017* (2013.01); *A61B 2017/00296* (2013.01); *A61B 2017/00411* (2013.01); *A61B 2090/08021* (2016.02)

(56) References Cited

U.S. PATENT DOCUMENTS

| | | | | |
|---|---|---|---|---|
| 2005/0143763 | A1* | 6/2005 | Ortiz | A61B 17/1114 606/153 |
| 2006/0142790 | A1* | 6/2006 | Gertner | A61N 1/36007 606/153 |
| 2007/0213749 | A1 | 9/2007 | Kogasaka et al. | |
| 2009/0287236 | A1 | 11/2009 | Bakos et al. | |
| 2010/0191264 | A1* | 7/2010 | Kassab | A61B 17/3417 606/153 |
| 2011/0295055 | A1* | 12/2011 | Albrecht | A61B 17/00234 604/9 |
| 2014/0236064 | A1 | 8/2014 | Binmoeller et al. | |
| 2015/0327853 | A1 | 11/2015 | Aronhalt et al. | |
| 2016/0100971 | A1* | 4/2016 | McGuckin, Jr. | A61F 2/04 604/8 |
| 2020/0337706 | A1* | 10/2020 | Truckai | A61B 17/3205 |

OTHER PUBLICATIONS

International Search Report Corresponding to PCT/EP2022/057913 mailed Jul. 13, 2022.

Written Opinion International Search Report Corresponding to PCT/EP2022/057913 mailed Jul. 13, 2022.

* cited by examiner

APPARATUS AND METHOD FOR ENDOSCOPIC ANASTOMOSIS OF THE STOMACH AND THE BOWEL

The invention is directed to apparatus and a method for anastomosis of the stomach and bowel, for example, using such an apparatus for the treatment of obesity and/or diabetes of a patient. Some non-limiting aspects relate to an endoscopic apparatus and method.

It is known in the prior art to use minimally-invasive implantable devices for the treatment of obesity and diabetes which hinder parts of the intestines, particularly the duodenum, from absorbing nutrients.

Many minimally-invasive implants suffer from the problem that the stomach and bowel and especially the pylorus are a very active area of the digestive tract. Therefore, some implants can be shifted or misaligned and/or only provide a short term solution.

A minimally-invasive permanent solution for the treatment of obesity has been proposed. A possible solution is offered by bypassing a portion of the intestines like the duodenum in order to address nutrient uptake.

Bypassing a portion of the intestine without laparoscopic surgery allows obese patients a faster recovery without external and abdominal incisions or scarring and wound infections. However, significant technical challenges remain in conducting minimally-invasive surgery in a safe and effective manner, without risk of injury to adjacent tissue or important organs, without risk of tearing tissue of the stomach or bowel, and without risk of post-operative leakage from the gastro-intestinal tract.

It would be desirable to address one or more of the above issues.

Aspects of the invention are defined in the claims.

In a first aspect, the invention provides apparatus for endoscopic anastomosis of the stomach and the bowel of a patient to allow food to bypass the duodenum and optionally a portion of the jejunum. The apparatus may optionally be configured to facilitate an endoscopic procedure, through only a single (e.g. natural) body orifice.

The apparatus comprises one or more of: a tube insertable into the stomach, the tube having a proximal end and a distal end; surgical apparatus which is deployable at the distal end of the tube and is at least partially, preferably completely, insertable through the tube; and/or at least one operating element connected or connectable to the surgical apparatus for operating the surgical apparatus from the proximal end. The surgical apparatus is configured for establishing anastomosis between a first area of the stomach and a second area of the bowel.

The distal end refers to the insertable end of the apparatus at which the surgical apparatus is deployable.

The proximal end refers to the end opposite to the distal end, which the surgeon will operate during the minimally invasive anastomosis procedure.

The apparatus is preferably insertable through a patient's natural body orifice, preferably the mouth.

The operating element preferably comprises an internal tube which can be arranged concentrically inside the tube.

The tube and/or internal tube preferably comprise an opening in the region of the distal end and an opening in the region of the proximal end which are connected by a channel or a cavity.

The surgical apparatus is preferably partially insertable into the tube or internal tube.

In particular preferably the surgical apparatus is completely movable through the tube or internal tube.

The operating element is preferably concentrically enclosed by the tube.

At least parts of the operating element are preferably movable relative to the tube along or rotatable around the longitudinal direction of the tube.

The surgical apparatus is preferably designed to establish close contact of the first area of the stomach and second area of the bowel.

The apparatus preferably comprises at least one imaging element, in particular a radiopaque and/or metallic element, preferably located at the distal end of the tube and/or operating element.

The tube and/or internal tube are preferably radially essentially immovable so that the cavity cannot be blocked by bending of the tube and/or internal tube.

The tube and/or internal tube may comprise materials such as stainless steel, titanium, platinum, iridium, barium, tungsten and/or plastics, in particular thermoplastics such as silicones, polyetheretherketone, polyamides, fluoropolymers, polyvinylchloride and/or polyurethane.

The apparatus is also preferably hydrophilic due to a coating. This makes insertion into a body passage easier and atraumatic. Furthermore, the coating increases the sliding properties of the apparatus.

Additionally or alternatively to any of the above, the surgical apparatus can comprise a cutting device for cutting tissue, optionally a cutting device which is rotatable in the direction along the circumference of the tube, and in particular optionally allows for the removal of tissue from the first area of the stomach and/or the second area of the bowel through the tube.

Preferably the cutting device is arranged or arrangeable concentrically around the longitudinal axis of the tube.

The cutting device can be suitable for cutting through the edges of the first area and/or second area. Multiple cutting devices can be conceived for cuts with different lateral profile sizes.

The cutting device can preferably cut only the outer edges of the first area and second area. A cut along the edges allows an easier removal of cut tissue through the tube.

The operating element preferably comprises a control element for operating the cutting device.

The control element and/or operating element are preferably torsionally stiff.

Torsionally stiff means that the transmission of torque is preferably substantially 1:1. Thus, the control element is preferably configured such that rotation in at least one direction of the control element at the proximal end through an angle results in substantially the same rotation through the angle at the distal end. Thus, the control element and/or operating element can be rotated from the proximal end.

Additionally or alternatively, the operating element may be axially movable. The apparatus may comprise a mechanism for translating rotation movement to linear movement, or vice versa.

Additionally or alternatively to any of the above, the cutting device can be convertible between (i) a stowed configuration for introduction to the first and/or second area, the stowed configuration having a first lateral profile about an axis of the tube; and (ii) a deployed configuration for operative cutting of tissue, the deployed configuration having a second lateral profile about an axis of the tube larger than the first lateral profile.

The second lateral profile may have a predetermined size (e.g. a fixed size). The cutting device may be configured to cut tissue when in the deployed configuration of predetermined (e.g. fixed) size.

The cutting device (optionally of a type deployable to a laterally larger deployed configuration) may be mounted on a shaft, for example, a hollow shaft. The cutting device may be configured for cutting a closed loop shape aperture in tissue. Optionally the closed-loop shape extends around an axis of the shaft and/or around an axis of the tube.

The cutting device, when deployed for cutting, may have a cutting element and/or cutting surface facing towards the distal end of the tube. Additionally or alternatively, the cutting device, when deployed, may be configured for cutting tissue in a cutting direction towards the distal end of the tube.

Howsoever the cutting device is implemented, the control element can comprise means for converting the cutting device into the deployed configuration and stowed configuration and separate means for operating the cutting device once deployed.

The cutting device is preferably reversibly convertible from the stowed configuration to the deployed configuration.

A selectively convertible cutting device can preferably be stowed inside the tube and/or internal tube in the stowed configuration.

The enclosed area by the lateral profile of the cutting device in the deployed configuration is optionally at least twice, optionally at least three times, optionally at least four times, the enclosed area of the lateral profile in the stowed configuration.

The lateral profile of the cutting device is preferably radially expanded from the longitudinal axis of the tube in the deployed configuration and radially collapsed in the stowed configuration.

The deployable cutting device can allow for a greater lateral profile cutting area than the lateral profile of the tube which has to be small enough to be inserted through the oesophagus.

The cutting device is preferably radially expandable in a closed-loop shape in particular preferably a circular or elliptical shape.

The cutting device may optionally comprise a reversibly rollable blade element that is convertible between an unrolled state and a rolled-up state. The blade element can assume a predetermined size and/or shape, preferably a circular shape, outside the tube in the deployed configuration and can be placeable in the cross-section of the tube in the stowed configuration. In the stowed configuration the blade element can have a spiral lateral profile. The cutting device may be formed from only one blade element.

The rollable blade element can preferably be converted from the stowed to the deployed configuration and vice versa by means of the control element.

It is conceivable that the cutting device is composed of at least two segments which are only functional when the cutting device is converted to the deployed configuration. For example, the cutting device may comprise segments that collapse into an overlapped space-saving configuration, and deploy side-by-side in a larger shape.

A cutting device is conceivable which can be converted to the second lateral profile only by rotational movement relative around the longitudinal axis of the tube. For example, the cutting device may collapsible by winding into a spiral shape, and deployable by unfurling the spiral.

A cutting device can be conceived that is only moving in radial direction to the tube when being converted from the stowed configuration to the deployed configuration and vice versa.

As an alternative to a cutting device a dilatation element is also conceivable, in particular for the dilation of the stomach.

The cutting device can comprise at least one holding device. The holding device can restrict and/or guide radial expansion of the cutting device to a predetermined size when entering the deployed configuration, and/or guide radial collapsing of the cutting device to the collapsed configuration.

The holding device can comprise a detachable and/or releasable latch. The latch preferably latches when the predetermined size of the cutting device through expansion is reached.

The latch is preferably releasable by rotation and/or translation of means of the control element.

Howsoever, the cutting element is implemented, the cutting device can be configured for cutting tissue from a first side, and the apparatus further comprises a counter element deployable on an opposite second side of the tissue. Optionally, the counter element may serve and/or be configured to (i) protect surrounding tissue on the second side from the cutting device, and/or (ii) provide a cutting board for the cutting device, and/or (iii) co-operate with the cutting device to capture cut-out tissue for removal through the tube.

Protecting adjacent tissue can provide significant advantages in terms of safety for the patient. When cutting tissue, there is less risk of injury, because the operative portion of the cutting element can be covered or shrouded by the counter element.

By fixing the tissue from both sides, the incision is not dependent on the skills of a surgeon and the surrounding tissue can be protected.

In some embodiments, the cutting device is positioned distally of the counter element, at least in the deployed configuration of the cutting device.

The tube's lateral profile can be larger than a lateral profile of a cut by the cutting device. The tube can preferably be designed to cover an incision by the cutting device in the first area protectively. Leakage of fluid from and into the stomach can preferably be prevented.

The tissue to be cut is preferably clamped by the surgical apparatus so that a cutting movement with the cutting device only comes into contact with the tissue to be cut. Force transmission to surrounding tissue is preferably optimized by applying pressure to the tissue.

The counter element can be convertible between (i) a stowed configuration for introduction to the first and/or second area, the stowed configuration having a first lateral profile about an axis of the tube; and (ii) a deployed configuration having a second lateral profile about an axis of the tube larger than the first lateral profile.

In some embodiments, this enables the counter element to be passed through a small aperture to an opposite side of the tissue, and deployed on the opposite side, without risk of tearing the tissue.

The counter element can preferably be arranged and/or is arrangeable concentrically to the tube, preferably at the distal end of the tube. The counter element in the deployed configuration preferably encloses at least the same area as the second lateral profile of the cutting device.

The counter element can be connected or connectable to the cutting device.

The counter element can be connected or connectable to the distal end of the tube and/or operating element.

The counter element can preferably convert from the stowed configuration to the deployed configuration and vice versa by means of the operating element.

The conversion can be carried out by a translational movement along the longitudinal axis of the operating element and/or a rotation along the circumference or profile of the operating element. The counter element in the deployed configuration can be unfolded and/or expanded and the counter element in the stowed configuration can be folded and/or contracted.

The counter element in the stowed configuration can preferably be inserted and exerted through the tube and/or internal tube.

The cutting device can comprise a knife element and/or a piercing element and/or an electrical or optical ablation element. The cutting element may be movable during cutting, in a rotary movement following a curvature and/or in an axial direction.

Rotation of means of the control element optionally allows a rotation of the cutting device. The rotation of means of the control element can in particular preferably cause helical rotation of the cutting device along the longitudinal axis of the apparatus.

A cutting device that cuts point by point is also conceivable.

In particular a cutting device using electrical ablation, for example, radiofrequency ablation, is conceivable. A cutting device using radiofrequency or microwave ablation preferably allows for a less traumatic procedure.

A point by point cutting device is preferably rotatable around a longitudinal axis of the control element in a closed-loop, in particular preferably in a circular or elliptical manner.

The apparatus can comprise a cutting device for cutting the first area and a cutting device for cutting the second area. The circumference or lateral profile of the cutting device for the first area of the stomach is preferably smaller than the circumference or lateral profile of the cutting device for anastomosis between the first area and second area.

Additionally or alternatively to any of the above, the apparatus can comprise at least one insertable element insertable through a tissue wall at the first and/or second area, the insertable element having a stowed configuration for introduction through the tissue wall, and being expandable to a deployed configuration for overlapping, at least partially tissue of the tissue wall.

The surgical apparatus can comprise the insertable element. The deployed configuration and a stowed configuration of the insertable element can be reversibly converted into each other by means of the operating element.

The insertable element in the deployed configuration can be rotated, unfolded and/or expanded. The insertable element in the stowed configuration can be rotated reversely, folded and/or contracted. An at least partially inflatable and deflatable insertable element could also be conceived.

The cross-section of the insertable element in the deployed configuration preferably encloses at least the same area as the second lateral profile of the cutting device.

In the stowed configuration the insertable element can be inserted through smaller openings of tissue. The entry opening can therefore be smaller and the apparatus can allow a less traumatic and/or invasive surgical procedure, with less risk of tearing tissue.

The insertable element is preferably convertible from the deployed configuration to the stowed configuration by rotational and/or translational movement of the operating element from the proximal end of the apparatus.

The insertable element in the deployed configuration preferably has an increased radial or lateral dimension. In particular preferably the insertable element can have a greater cross-sectional surface area in the deployed configuration.

The insertable element can preferably protectively cover punctured tissue in the deployed configuration and prevent leakage.

The operating element may comprise an extension element which is attached to the insertable element. It is conceivable that the extension element can convert the insertable element from the deployed configuration into the stowed configuration and vice versa.

In one conceivable embodiment, retraction of the extension element can press the insertable element against a counter element or the operating element so that the insertable element assumes the stowed configuration.

Extension of the extension element can convert the insertable element into the deployed configuration.

The insertable element may comprise stainless steel, titanium, nickel titanium, tungsten, a fluoropolymer layer, thermoplastics, especially polyetheretherketones.

The counter element can preferably be placed in the proximal direction of the insertable element.

The cross-section profile area of the counter element in the deployed configuration is preferably equal to at least that of the cross-section profile area of the insertable element in the deployed configuration.

The insertable element can be movable relative to the tube from a distal end of the tube, preferably in the longitudinal direction of the tube. The insertable element is preferably movable by rotation or translation movement of the operating element.

The insertable element is preferably movable relative to the remainder of the apparatus by the operating element.

The internal tube or complete operating element is preferably also movable relative in the longitudinal direction of the tube.

The operating element can be inserted through the first area of the stomach.

The insertable element can preferably be converted into the deployed configuration after introduction through a tissue wall.

The insertable element is preferably pullable or retractable in the deployed configuration so that the second area can be pulled towards the first area to establish close contact.

The insertable element can be folded radially outward from the longitudinal axis of the tube from the stowed configuration into the deployed configuration, preferably in an umbrella shape, in particular preferably folded around a fixed point at the distal region of the insertable element.

An insertable element in the stowed configuration can be conceived that increase in lateral profile width from its distal end to the proximal end.

The distal region of the insertable element in the stowed configuration can comprise a second cutting device for piercing and/or cutting tissue.

The cut area of tissue by piercing with the second cutting device is preferably smaller than the cut area of tissue by the cutting device.

The second cutting device can preferably be used for piercing and/or cutting by translational movement in a direction parallel to the longitudinal axis of the apparatus.

The insertable element, being movable relative to the tube, can enable the insertable element to pierce tissue of the stomach and/or bowel in the stowed configuration with the second cutting device.

The insertable element can also be conceived to comprise the cutting device at its proximal end.

It would be conceivable cutting with the insertable element would be mechanically operable by pulling and/or rotating the insertable element, preferably by means of the operating element.

A combination of at least two of:

the insertable element in the deployed configuration; the counter element in the deployed configuration; and the cutting element, are adapted to form an interface to enclose tissue. For example, the insertable element and the counter element may have a lateral profile greater than the lateral profile of the cutting device.

By enclosing tissue with the counter element and insertable element the tissue can preferably be cut in a section of the first area and/or second area.

The cutting device can be located in between the counter element and the insertable element. The cutting device can also be located on the distal end of the counter element and/or the proximal end of the insertable element.

The lateral profile of the cutting device in the deployed configuration can correspond essentially to the diameter of the anastomosis to be obtained. The anastomosis to be obtained is preferably large enough to replace the function of the pylorus. Hence, the diameter of a preferably circular cutting device for establishing the anastomosis is preferably between 1 cm and 6 cm.

The pylorus can preferably be sutured or stapled shut after the procedure so that food can be drained exclusively through the anastomosis. In order to account for missing muscles like the pyloric sphincter at the anastomosis the anastomosis preferably has a greater lateral area than the pylorus.

The insertable element, the counter element and/or the cutting device can be designed to hold the removed tissue and remove it through the tube.

The insertable element can preferably cover a cut in proximal direction when in the deployed configuration. For this reason the insertable element is preferably foldable radially outward from the longitudinal axis of the tube. The insertable element can preferably prevent fluid from passing through the point of entry of the insertable element.

The insertable element can comprise a concave curvature, preferably in the deployed configuration. The insertion element can preferably cover the entry opening in the tissue with the concave curvature on the tissue.

The operating element can comprise a folding device.

The insertable element is preferably foldable around a fixed point at the distal region of the insertable element by the folding device, such as hinges.

The folding device can preferably be operated from the proximal end of the apparatus to convert the insertable element from the deployed to the stowed configuration.

The insertable element in the stowed configuration can preferably be placed inside the operating element or internal tube.

The apparatus can comprise an implantable stent comprising a non-return mechanism convertible between an open state and a closed state. The closed state can prevent passage of fluid and an open state can enable crossing of fluid. The implantable stent can comprise a non-return valve which can enable only one-directional passage of fluid.

In the area of the digestive tract, many movements and dilations are necessary for nutrient absorption and digestion. A non-return mechanism is advantageous so that the sensitive enzymatic and acid balance cannot be negatively affected by the transferal of fluid from the bowel into the stomach and vice versa.

The stent can preferably be placed in vicinity of the anastomosis opening. The stent can be placed at least partially inside the anastomosis opening. The stent is preferably placed inside the anastomosis opening protruding into the stomach and/or the bowel.

In an embodiment to prevent leakage between the stomach and bowel the stent can comprise a balloon which can be filled with a fluid in order to close the anastomosis opening and emptied in order to open the anastomosis opening. The fluid for the balloon is preferably supplied by a fluid reservoir which can be reversibly emptied and filled. The fluid reservoir is preferably placed in the stomach or bowel.

The balloon can preferably selectively be filled and emptied with fluid, preferably by control of an external device.

The non-return valve may comprise at least one sealing element, preferably a flap.

The sealing element of the non-return valve can preferably be pressed into the seal seat by the flow pressure of the flowing fluid from the bowel to the stomach. In an alternate embodiment the non-return valve includes a tubular polymer.

The tubular polymer is preferably insertable directed in the direction of the digestive pathway. The tubular polymer can comprise multiple sealing elements. The sealing elements of the tubular polymer can preferably be located along the inner lateral profile of the tubular polymer. The sealing elements are preferably circular and/or helical.

The tubular polymer can preferably only allow fluid to pass in one direction. The tubular polymer is preferably designed so that a passage can be widened by fluid when passing from the stomach to the bowel. Otherwise, the passage is preferably closed.

The passage of the tubular polymer from the bowel to the stomach can preferably be closed by radial narrowing of the tubular polymer. Radial narrowing of the tubular polymer is preferably optimized by choice of the material, thickness, length, and/or placement in the digestive pathway. The tubular polymer can preferably be crumpled up in order to block the passage of fluid from the bowel to the stomach.

The tubular polymer can comprise silicone, polyurethane, polyester polyethylene terephthalate, fluoropolymer, and/or polyamide.

The apparatus can comprise a pressure device for selectively applying a negative pressure to at least one area in the tube and/or a retaining element in an area at a distal end of the apparatus for retaining a distal end of the apparatus to tissue.

The pressure device can apply a negative pressure creating suction on the distal end of the tube and/or operating element.

In particular the pressure device can preferably apply a pressure in a cavity of the operating element, in particular preferably at the opening of the internal tube.

The distal end of the apparatus can be removably attachable to the targeted tissue in the first area and/or second area through the pressure device.

Through attachment of the apparatus the cut can be more precise and the risk of injury is minimized.

The tube and/or internal tube are preferably radially stiff so that it is not deformable by the pressure device.

The retaining element can preferably attach to the stomach mucosa and/or the bowel.

In some embodiments, the tube can have a length of 30 cm to 100 cm, in particular 45 cm to 60 cm and a diameter of 4 mm to 20 mm, in particular 6 mm to 14 mm.

The diameter and/or length of the apparatus are preferably at least large enough to extend from a patients mouth to the second area of the bowel for a minimal-invasive procedure.

In addition to or alternatively to any of the above, the apparatus can comprise a fixation device, for example, a suture device and/or a stapling device. The fixation device can be designed to suture and/or staple the outer edges of the first area and the second area, preferably in a predetermined manner, in particular preferably in a circular manner.

A sutured and/or stapled anastomosis may prevent leakage more reliably than a stent, because the movement in the digestive organs can be better accommodated without risk of dislodgement.

The fixation device can be designed to be used on both sides of the tissue to be cut, adjacent to the surface of the tissue, in the first area and/or in the second area.

The fixation device can preferably be arranged in proximal direction behind the entry opening of the tissue or in distal direction in front of the entry opening. The fixation device can be arrangeable connected or connectable to the insertable element, cutting device and/or counter element.

The fixation device can preferably allow for suturing and/or stapling while tissue is clamped by the counter element and the insertable element.

The fixation device can be arrangeable concentrically around the tube.

The fixation device is preferably designed to connect both the first area stomach wall and the second area bowel wall with sutures or staples by puncturing both areas.

The fixation device is preferably insertable and exportable through the tube and/or internal tube.

It is conceivable that the fixation device is rotatable in a circumferential direction to the surgical apparatus.

It can be conceived that the fixation device can be convertible between a stowed configuration and a deployed configuration. The fixation device can have an increased second lateral profile around a longitudinal axis of the tube in the deployed configuration than the first lateral profile in the stowed configuration.

The anastomosis and/or cut-shape and/or fixation (e.g. suture or staple) pattern can have a closed-loop shape that may be circular, or elliptical, or any other closed-loop form, whether symmetric or asymmetric.

In some embodiments, the fixation device can comprise fusing means, wherein the fusing means can be designed to cause fusion of tissue of the first area of the stomach and the second area of the bowel, by applying a pressure and heating, preferably radio-frequency heating, at least on the edges of the first area and the second area.

The fusing means can be designed to exert and/or keep radial force to keep the communication between the stomach and bowel open. The radial force can be applied by expandable elements such as balloons and or mechanical elements such as spikes. The fusing means preferably also comprise means for applying pressure to the tissue walls from both sides of the enclosed tissue.

The fusing means can preferably prevent leakage of the fused tissue interface.

Additionally or alternatively to any of the above, the device can comprise a second tube. A distal end of the second tube can be guidable from the stomach through the duodenum and connectable with the distal end of the tube across the stomach wall of the first area and the bowel wall of the second area.

The apparatus can comprise a guiding wire, wherein the tube and/or second tube can be advanced along the guiding wire to enclose the first area and/or second area.

The tube and/or second tube can preferably be advanced along the guiding wire by being concentrically arranged around the guiding wire.

As an alternative embodiment a guiding wire is conceivable which can be pierced through the first area and the second area less invasive. A guiding wire preferably only has a diameter of less than 1 mm.

The problem is further solved by a method for endoscopic anastomosis of the stomach and the bowel of a patient to allow food to bypass the duodenum and optionally a portion of the jejunum as previously described.

In a related aspect, the invention provides a method, optionally using apparatus with any one or more of the features described above, the method comprising the following steps:

- Insertion of an apparatus, preferably through the oesophagus, into the stomach and attaching to the stomach wall in the first area, preferably by applying a negative pressure;
- Piercing and/or cutting the stomach wall and deploying an insertable element outside of the stomach, preferably through unfolding and/or expanding the insertable element;
- Advancing a counter element, preferably with the cutting device connected to it, on the inside of the stomach to the first area;
- Clamping the stomach wall of the first area between the insertable element and the counter element and cutting a hole into a section of the first area with a cutting device;
- Preferably removing the cut-out stomach tissue between the counter element and the insertable element;
- Advancing the apparatus through the hole and locating the target location making up the second area for an anastomosis;
- Attaching to the outside of the bowel wall in the second area, preferably by applying a negative pressure;
- Piercing and/or cutting through the bowel wall and deploying the insertable element inside the bowel, preferably unfolding and/or expanding the insertable element in the second area;
- Pulling the insertable element to bring the first area into close contact with the second area;
- Advancing the counter element with the fixation device and clamping the first and second area between the counter element and the insertable element;
- Cutting a hole into a section of the second area with the cutting device and fixing (optionally stapling and/or suturing) the edges of the first area and second area together with the fixation device;
- Preferably removing the cut-out stomach and/or bowel tissue through the tube;
- After this procedure the counter element, fixation device and/or insertable element can be retrieved and the anastomosis can be inspected for size, shape and/or leaks.

In a preferred method the pylorus can be closed, for example sutured and/or stapled closed, so that the passage of food through the pylorus is no longer possible. All the ingested food must pass through the digestive tract, preferably through the anastomosis opening.

Finally, the apparatus can be removed from the patient's orifice, preferably the oesophagus.

In any of the above aspects, the apparatus may be configured, or the method performed, to create the anastomosis by insertion of the apparatus into the body via a single orifice. The single orifice may be a natural body orifice, for example, a mouth. Performing the procedure uniquely endoscopically, and avoiding the need for additional orifices, can enable the procedure to be less invasive than compared to multiple orifices used for laparoscopic surgery. In other embodiments, the apparatus may be used in combination with other laparoscopic tools.

Figure 2A:
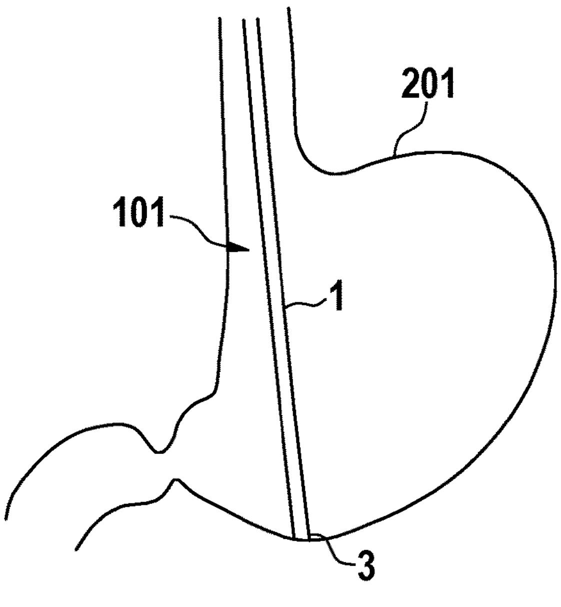
Figure 2B:
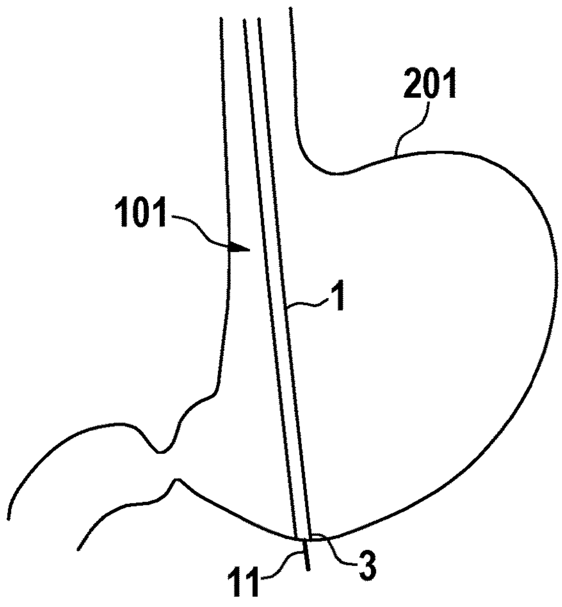
Figure 2C:
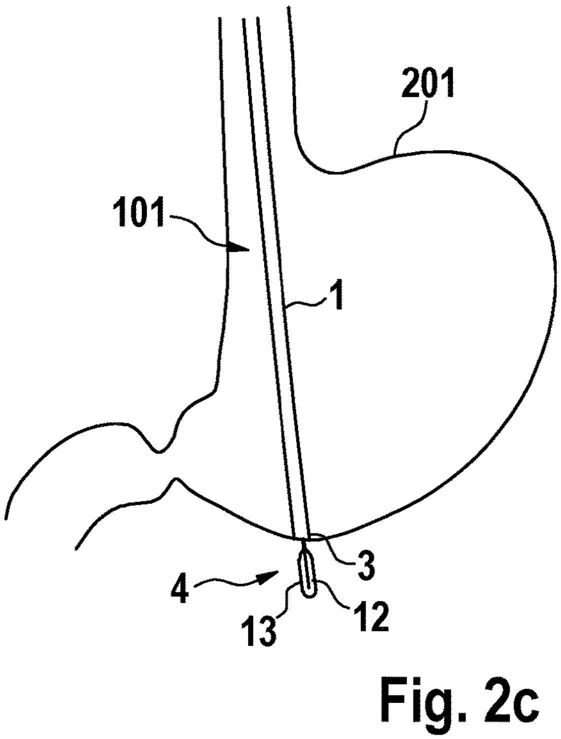
Figure 2D:
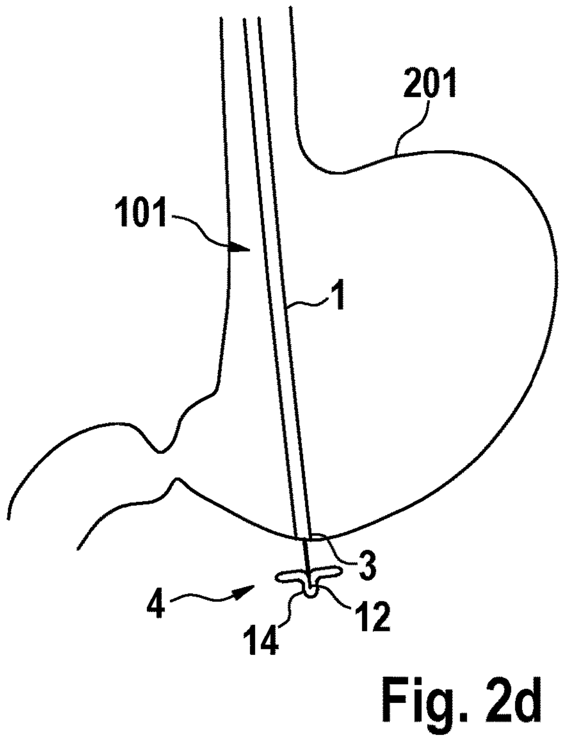
Figure 2E:
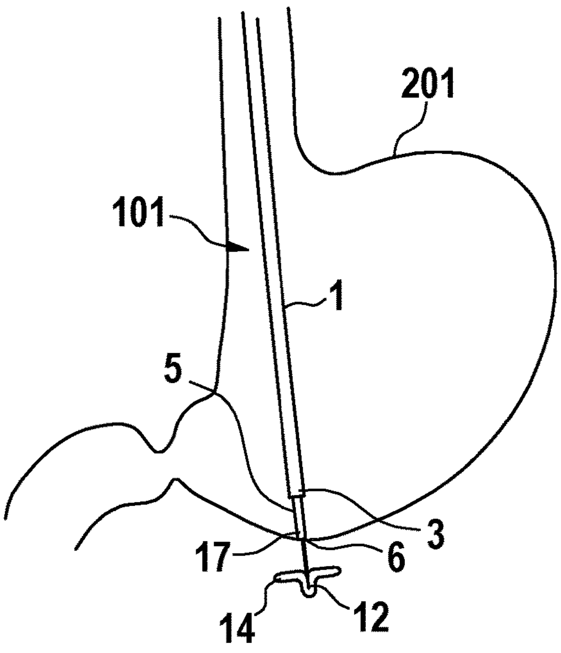
Figure 2F:
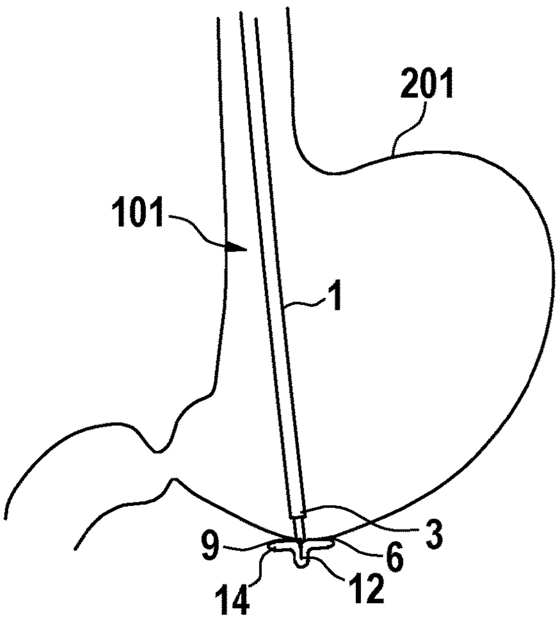
Figure 2G:
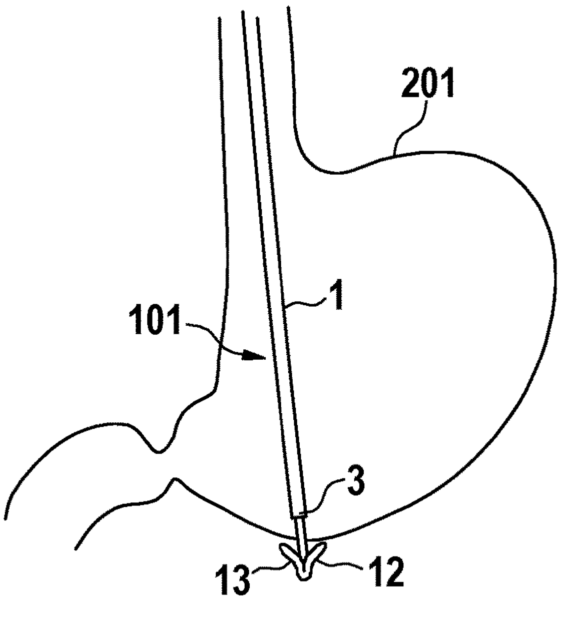
Figure 2H:
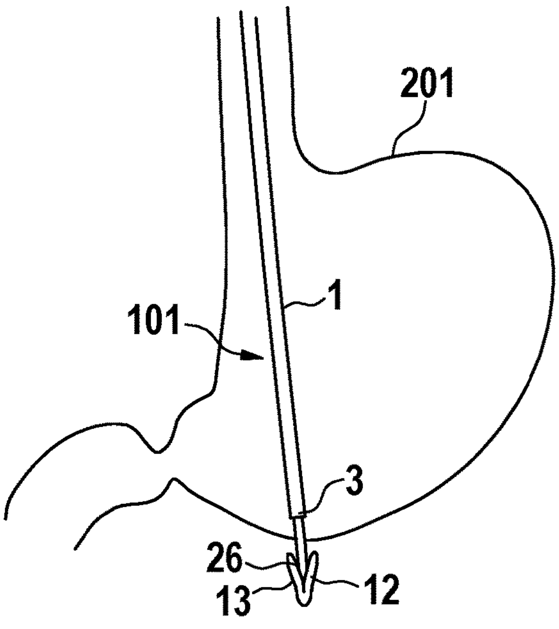
Figure 2I:
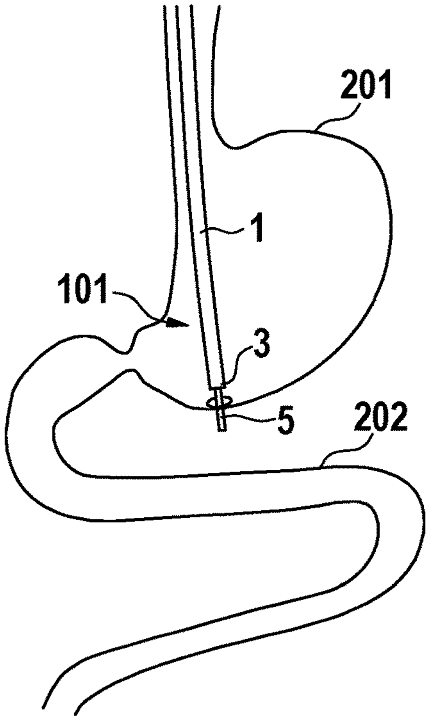
Figure 2J:
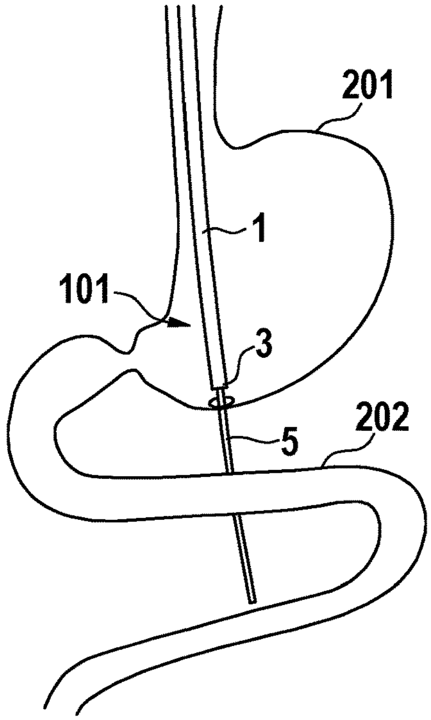
Figure 2K:
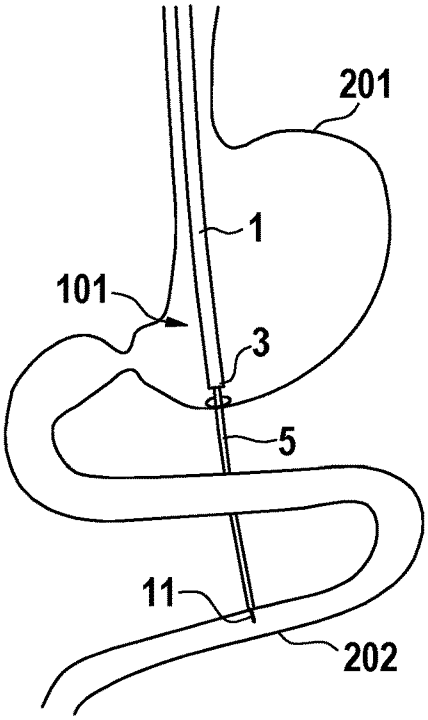
Figure 2L:
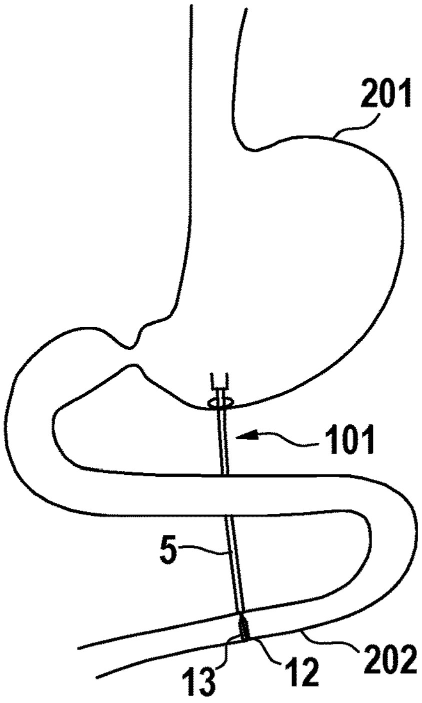
Figure 2M:
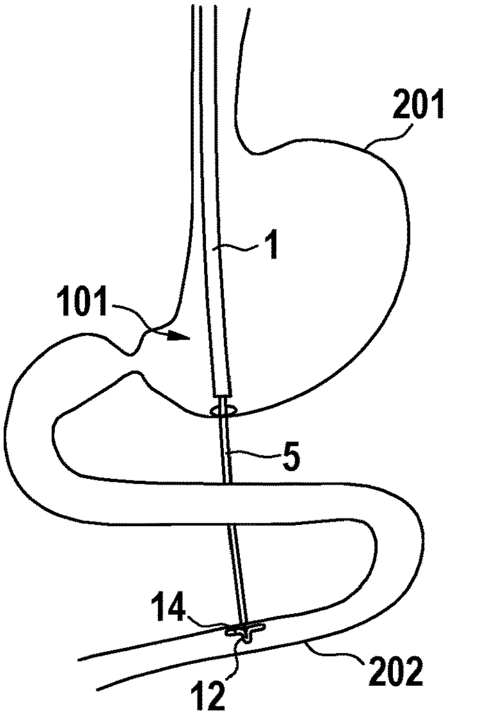
Figure 2N:
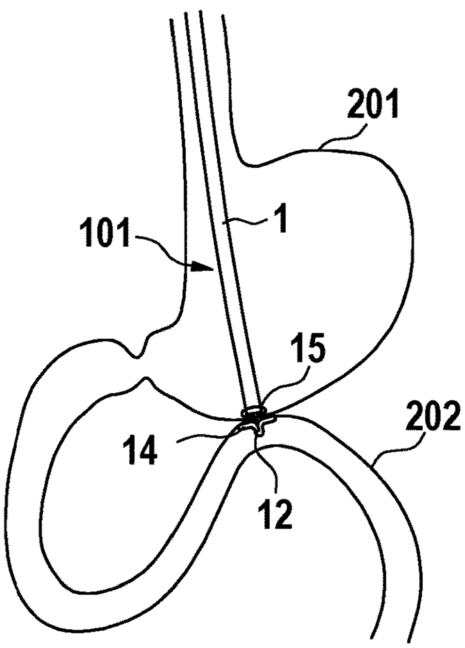
Figure 2O:
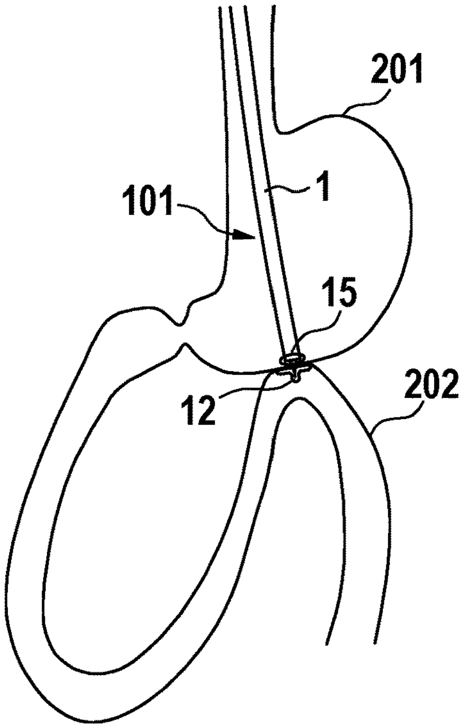
Figure 2P:
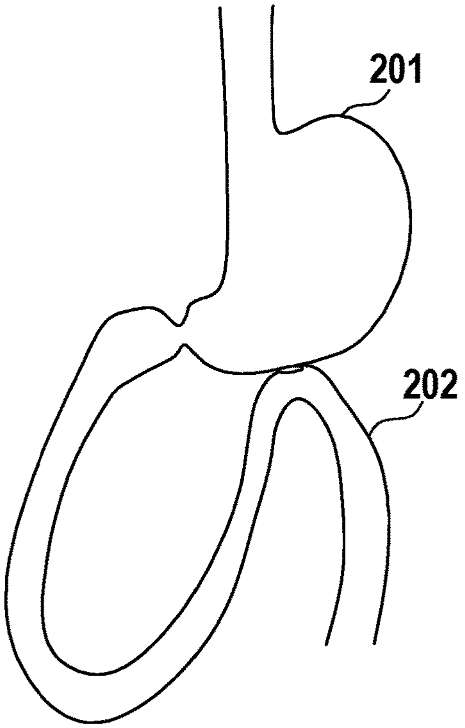
Figure 3A:
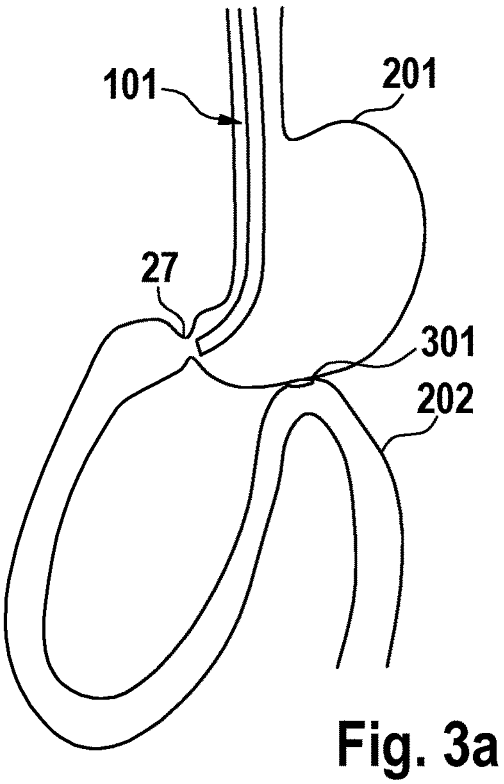
Figure 3B:
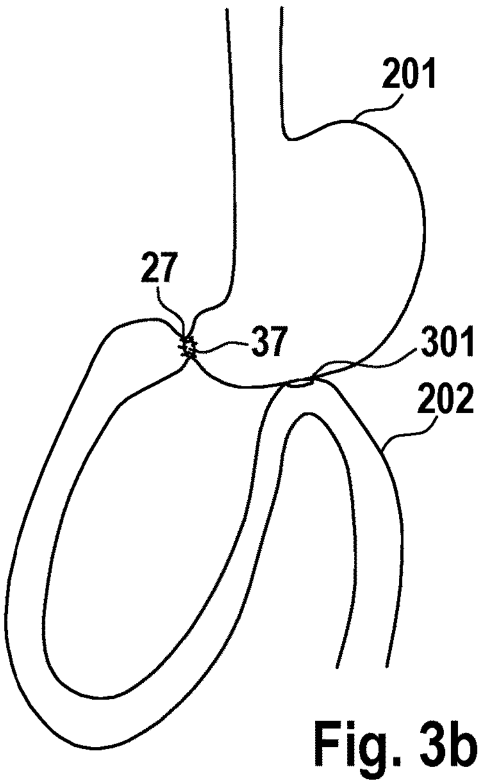
Figure 9A:
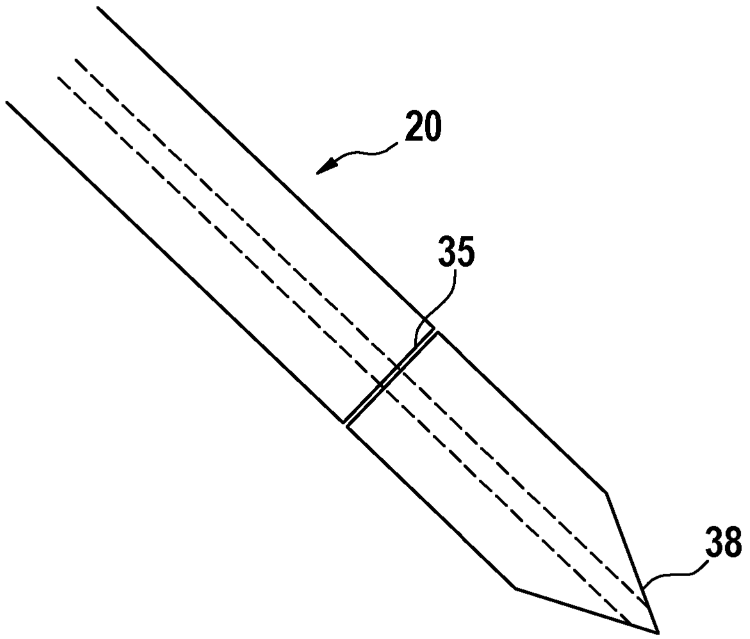
Figure 9B:
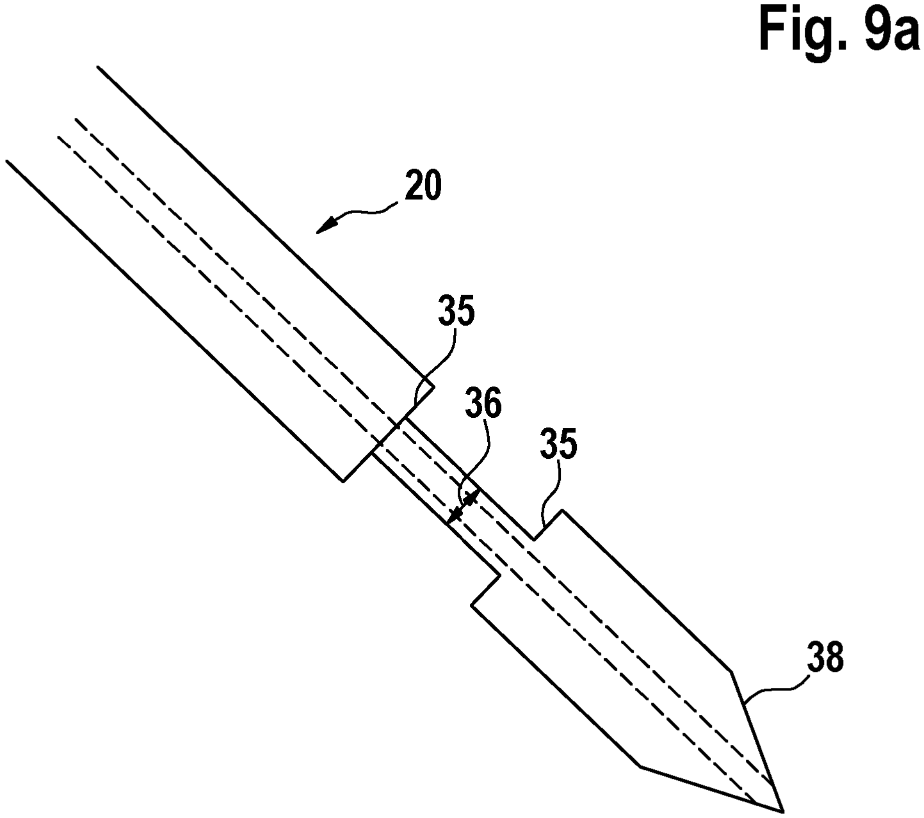
Figure 10:
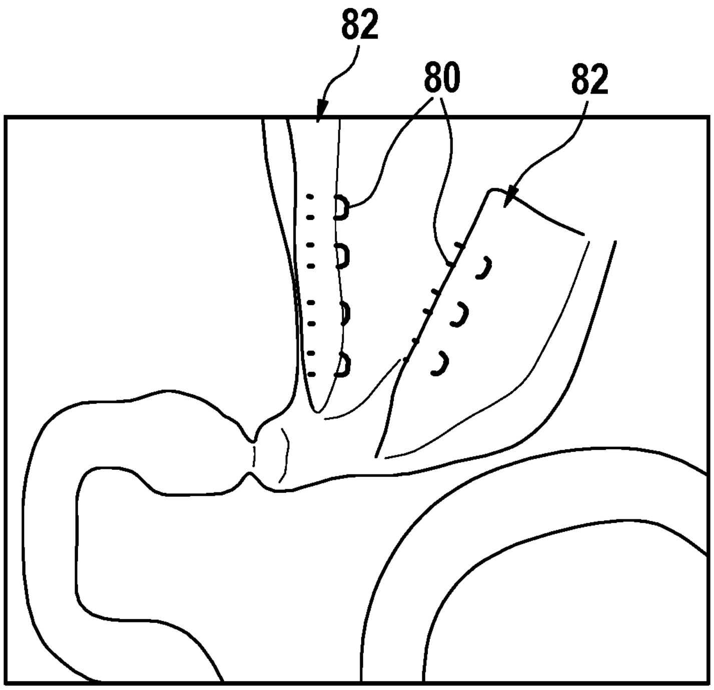
Figure 11:
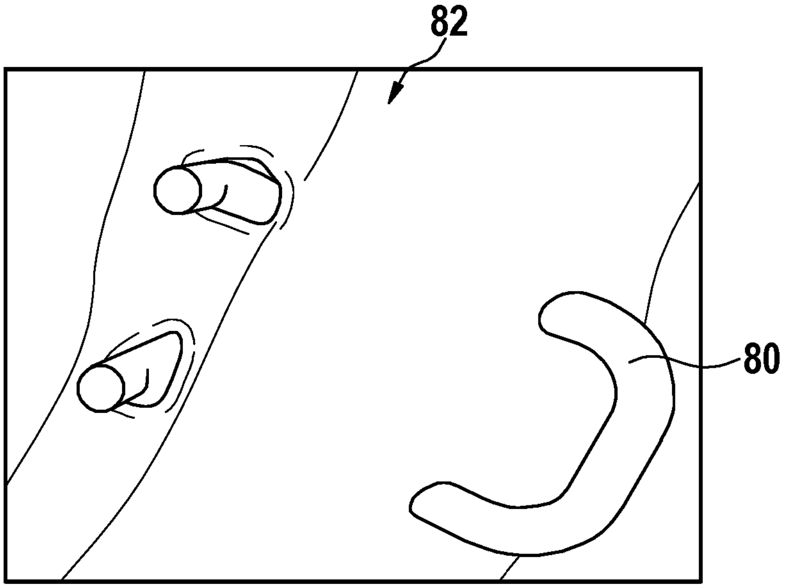

Non-limiting embodiments of the invention are now described, by way of example only, with reference to the accompanying schematic drawings, in which:

FIG. 1: shows an illustration of an anastomosis of stomach and bowel;

FIG. 2*a*-2*p*: show an endoscopic anastomosis of the apparatus with an insertable element;

FIG. 3*a*-3*b*: show a schematic illustration of closing the pylorus;

FIG. 4*a*-4*f*: show the cutting device in the deployed and stowed configuration;

FIG. 5*a*-5*h*: show the use of the apparatus with an insertable element in the stowed and deployed configuration cutting tissue with the counter element;

FIG. 6*a*-6*g*: show an alternative embodiment of the apparatus with an insertable element in the stowed and deployed configuration cutting tissue with the counter element;

FIG. 7*a*-7*g*: show another alternative embodiment of the apparatus with an insertable element in the stowed and deployed configuration cutting tissue with the counter element;

FIG. 8*a*-8*g*: show a surgical anastomosis of the apparatus using a guiding wire;

FIG. 9*a*-9*b*: show fusing means that can ride over a guiding wire to fuse tissue through heating and pressure;

FIG. 10 is a schematic partial section showing a technique for reducing stomach volume; and FIG. 11 is a schematic view showing a detail of FIG. 10 on an enlarged scale.

Referring to the drawings, FIG. 1 shows a schematic anastomosis 301 between the stomach 201 and the bowel 202. The anastomosis 301 allows food to bypass the duodenum and thus reduce the nutrient uptake. The anastomosis diameter can be in a range between 1 cm and 6 cm.

FIG. 2*a* shows the insertion of the apparatus 101 into the stomach over the mouth and oesophagus of a patient. After insertion the pressure device (not shown in the figures) a negative pressure can be applied in the tube 1 to attach the apparatus 101 at the distal end 3 of the tube 1 to the mucosa of the stomach 201 in the first area.

FIG. 2*b* shows the piercing the stomach wall by a piercing element 11. The piercing element 11 can pierce a hole into the stomach wall with a sufficient lateral profile to insert a surgical apparatus 4 in form of an insertable element 12 in the stowed configuration 13 into the pierced opening as can be seen in FIG. 2*c*. The insertable element 12 can be converted into the deployed configuration 14 by expanding radially outward. The insertable element 12 is expanded laterally outward by folding radially outward around a fixed point in distal region of the insertable element 12 in an umbrella shape. The lateral profile of the insertable element 12 is thus overlapping the lateral profile of the cut into the tissue which introduced the insertable element 12. The insertable element 12 can be deployed outside the stomach wall and cover the cut made to introduce the insertable element 12 as seen in FIG. 2*d*.

FIG. 2*e* shows that the cutting device 6 can be advanced to the distal end 17 of the operating element 5 at the first area. The cutting device 6 can be operated by rotation of the operating element 5 but also a translational movement can be conceived. FIG. 2*f* shows that the stomach wall in the first area is clamped by the deployed insertable element 12 and counter element 9. A hole can be cut into the first area by operating the cutting device 6 with the control element. It is conceivable that the cutting device 6 is attached or attachable to the insertable element 12 or the counter element 9. It could also be conceived that the cutting device 6 can be deployed independently from the insertable element 12 or the counter element 9. In this embodiment the cutting device 6 is located on the internal surface of the stomach 201. After the hole was cut in FIG. 2*g* the cut-out tissue 26 is clamped between the insertable element 12 and the cutting device 6 as seen in FIG. 2*h*. The cut-out tissue 26 can be removed through the tube 1 with the insertable device in the stowed configuration 13.

As shown in FIG. 2*i* the operating element 5 can be advanced through the cut-out tissue to locate the target location of the second area of the bowel 202 as seen in FIG. 2*j*. For this purpose the apparatus 101 may optionally comprise a camera.

The operating element 5 is movable relative to the distal end 3 of the tube 1 at least from the first area of the stomach 201 to the second area of the bowel 202.

Once the second area is located the operating element 5 can apply a negative pressure to attach the apparatus 101 to the second area and pierce it with a piercing element 11.

In FIG. 2*l* the insertable element 12 is introduced into the bowel through the pierced cut in the stowed configuration 13. It is also conceivable that the insertable element 12 comprises the piercing element 11 at its distal end in order to pierce tissue and being inserted at the same time.

In FIG. 2*m* the insertable element 12 is converted to the deployed configuration 14.

The operating element 5 and the insertable element 12 in the deployed configuration 14 can be pulled or retracted to bring the first area and second area into close contact. The insertable element 12 in the deployed configuration 14 serves to protect the enclosed and surrounding tissue and can prevent leakage. The cutting device 6 can be used to cut-out the clamped tissue between the insertable element 12 and the counter element 9. FIG. 2*n* and FIG. 20 show that the fixation device 15 can be advanced to fix, e.g. staple or suture, the bowel and stomach walls to create an anastomosis 301. In this embodiment the fixation device 15 is concentric to the operating element 5 and connected to the cutting device 6. However the fixation device 15 can be conceived to be connected or connectable to that counter element 9, the insertable element 12 and/or the operating element 5.

As seen in FIG. 20 the fixation device 15, the insertable element 12 and the cutting device 6 and can be retrieved through the tube 1. The cut-out tissue can be removed through the tube 1 with the insertable element in the stowed configuration 13.

The anastomosis 301 can be inspected for size, shape and leaks as and the apparatus 101 consequently removed as seen in FIG. 2*p*.

FIG. 3*a* shows the pylorus 27 which can be closed after successful creation of a permanent anastomosis 301 of the stomach 201 and jejunum of the bowel 202. The closing of the pylorus could be carried out by attaching the apparatus 101 to the proximal opening of the pylorus 27 and deploying a fixation device (not shown in the figures). As shown in FIG. 3*b* the pylorus 27 is closed by multiple sutures and/or staples 37. It would also be conceivable that the pylorus 27 is closed by an implantable stent.

Figure 4A:
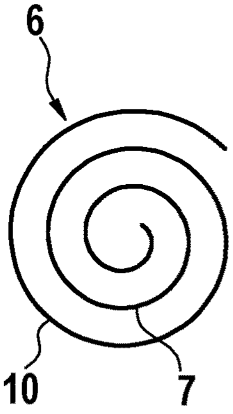
Figure 4B:
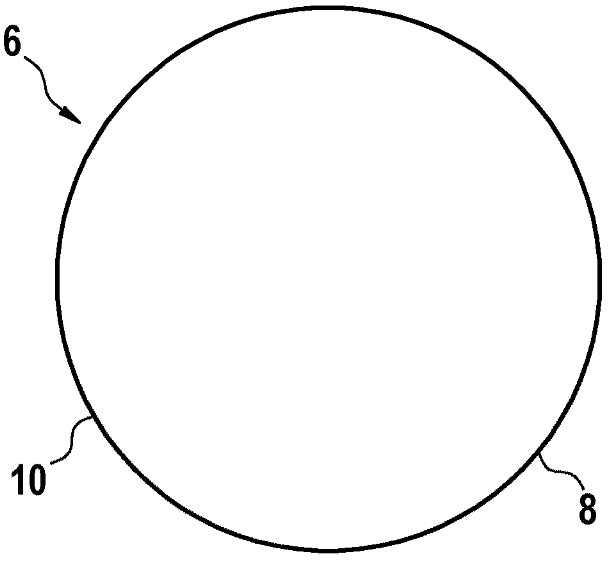
Figure 4C:
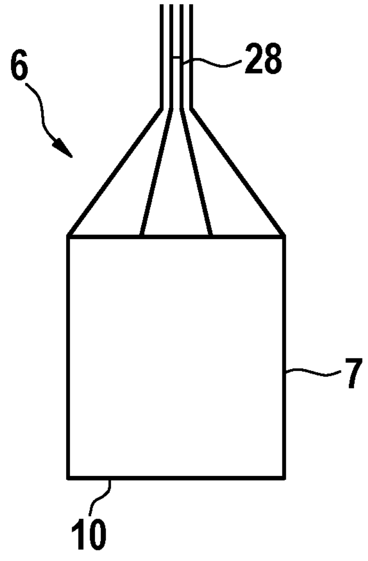
Figure 4D:
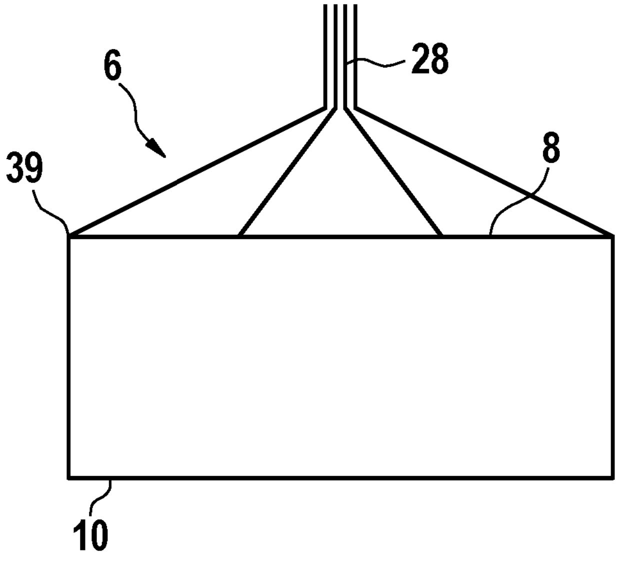

FIG. 4*a* and FIG. 4*c* show an embodiment of the cutting device 6 in the stowed configuration 7. FIG. 4*b* and FIG. 4*d* show the cutting device 6 in the deployed configuration 8. The cutting device 6 comprises a reversibly rollable or spirally furlable blade element 10 that is convertible between a stowed configuration 7 and a deployed configuration 8. The blade element 10 can be converted by rotation of the control element 28. However, also converting the cutting device 6 by relative movement of the control element 28 can be conceived. The blade element 10 in the deployed configuration 8 has a circular lateral profile as shown in FIG. 4*b*. The blade element 10 can preferably be rotated by a torsionally stiff control element 28 from the proximal end of the tube 1 (not shown in FIG. 4*a*-4*d*). The blade element 10 in this embodiment consists of only a single segment. The control element 28 is connected to the lateral distant regions 39 of the blade element 10 so that a reversible conversion between the deployed configuration 8 and the stowed configuration 7 can be carried out using the control element 28.

Figure 4E:
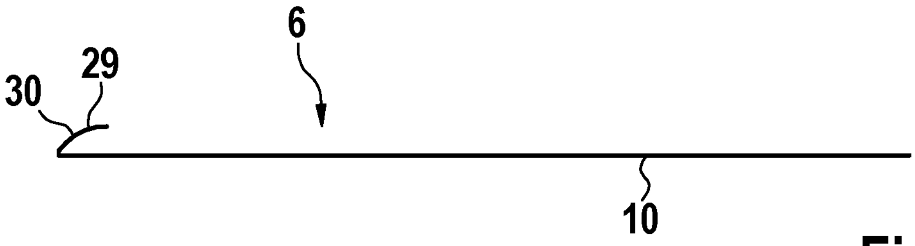
Figure 4F:
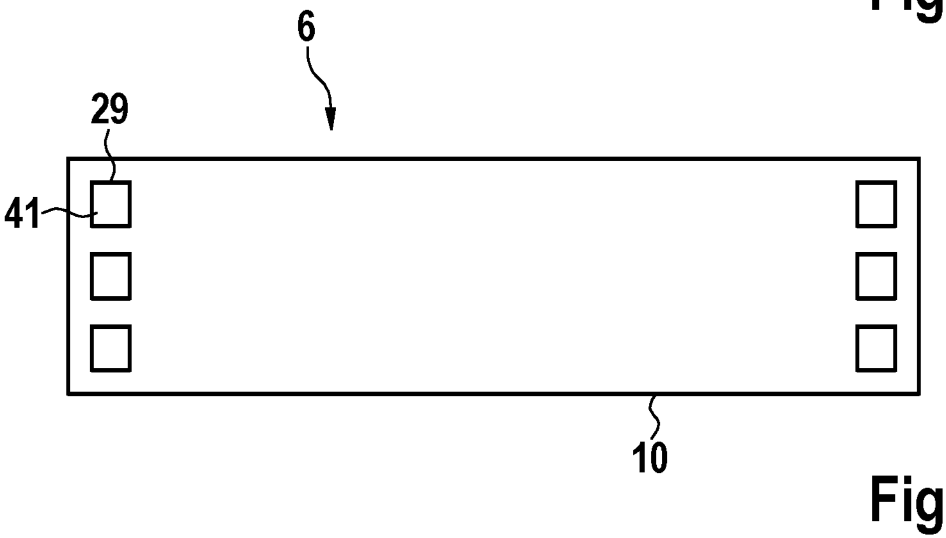

FIG. 4*e* and FIG. 4*f* show the rollable blade element 10 completely unrolled. As shown in FIG. 4*e* and FIG. 4*f* the cutting device 6 comprises a holding device 29 in form of one or more releasable latches 30 to latch the blade element 10 in its deployed configuration (8). The latch 30 latches into latch opening 41 when the predetermined size of the cutting device 6 through radial expansion is reached.

Figure 5A:
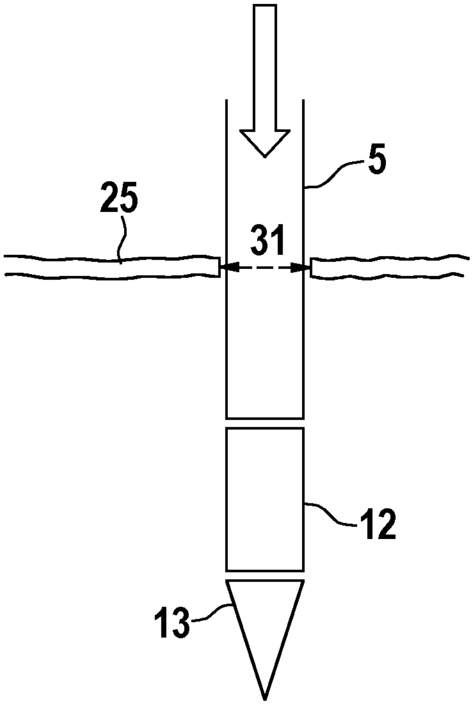
Figure 5B:
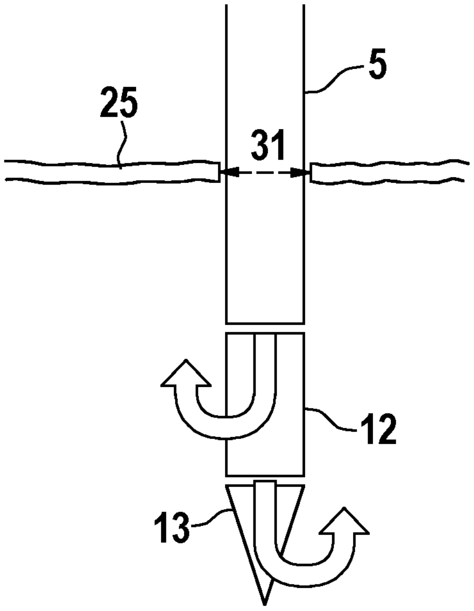
Figure 5C:
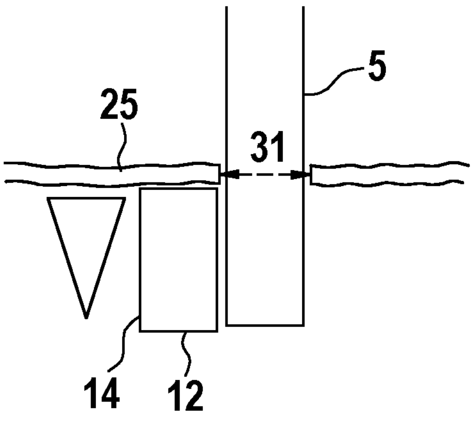
Figure 5D:
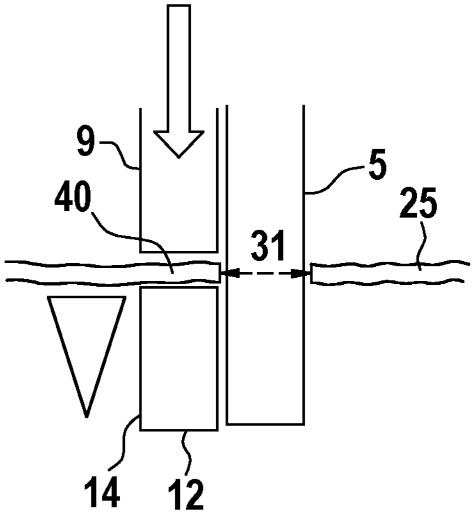
Figure 5E:
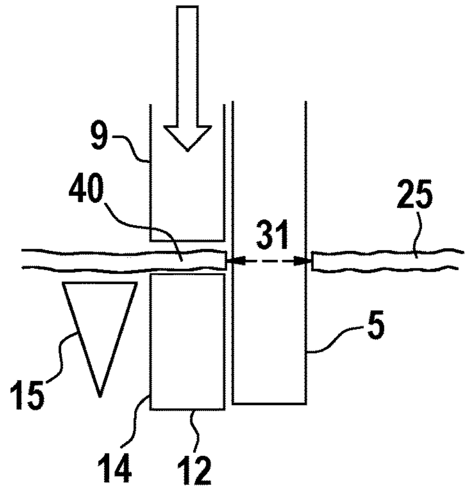

FIG. 5*a* shows a schematic representation of an embodiment of the insertable element 12 in the stowed configuration 13 that is introduced through a tissue wall 25 by an operating element 5. As shown by the arrows in FIG. 5*b* the insertable element 12 can be converted into a deployed configuration 14 with a greater lateral profile. The lateral profile is larger than the lateral profile of the entry opening 31. In FIG. 5*c* the insertable element 12 is in the deployed configuration 14 and can form a protective cover of the tissue from the other side of the tissue wall 25. The tissue wall 25 can be clenched with the insertable element 12 and the counter element 9 forming an enclosing interface 40 and cut by the cutting device (not shown in the figures) in the process as schematically shown in FIG. 5*e*.

By clenching the tissue wall 25 before engaging in the cutting process the cutting can be performed non-traumatically for the surrounding tissue.

The cutting device 6 can be arranged on the proximal side of the insertable element 12 in the deployed configuration 14 or on the distal side of the counter element 9 in the deployed configuration (not shown in FIG. 5*a*-*h*).

Figure 5F:
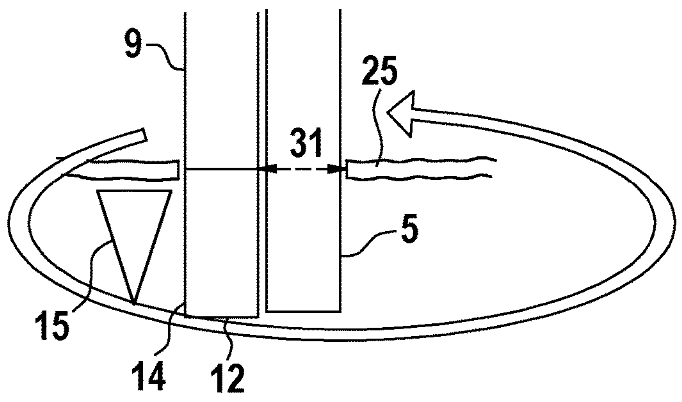

In this embodiment the fixation (e.g. suturing and/or stapling) device 15 is located on the insertable element 12 and allows for suturing the tissue wall 25 in the deployed configuration 14. It would also be conceivable that the fixation device 15 is located on the distal end of the counter element 9. As illustrated in FIG. 5*f* the insertable element 12 and counter element 9 can be rotatable around the entry opening 31 in order to cut and fixation (e.g. suture and/or staple) the anastomosis 301. It would be conceivable that only the fixation device 15 is rotatable around the cut tissue wall 25.

Figure 5G:
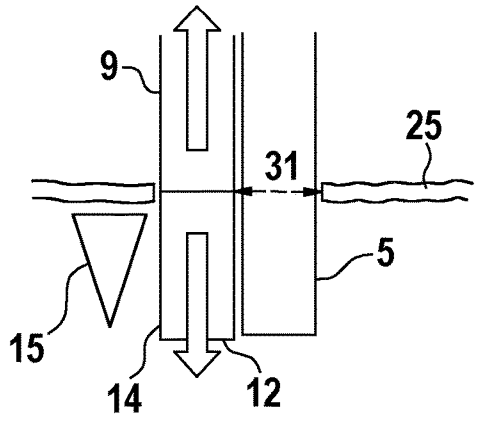
Figure 5H:
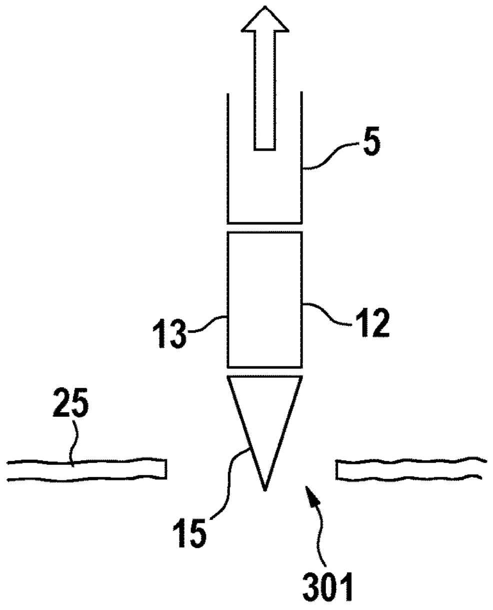

FIGS. 5*g* and 5*h* show that the insertable element 12 can be converted to the stowed configuration 13 after cutting and fixation is complete. In the final step the insertable element 12 can be removed in the stowed configuration 13 through the tube 1 with the cut-out tissue (not shown in FIG. 5*h*).

Figure 6A:
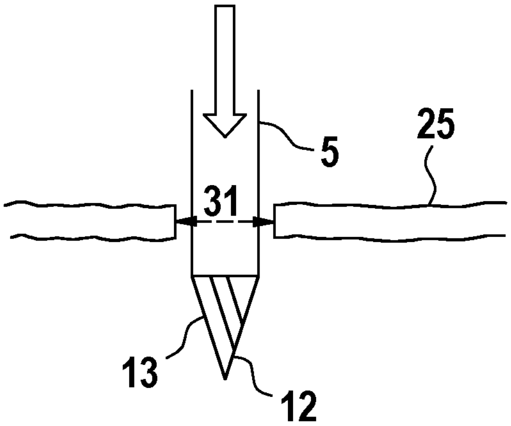
Figure 6B:
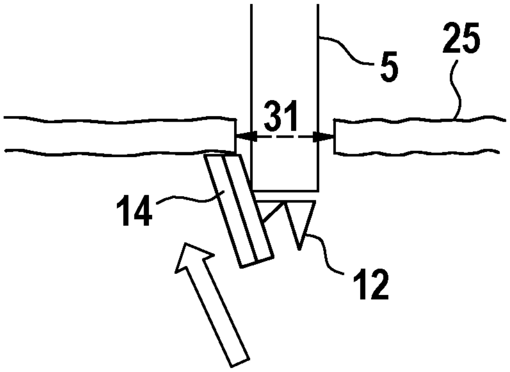
Figure 6C:
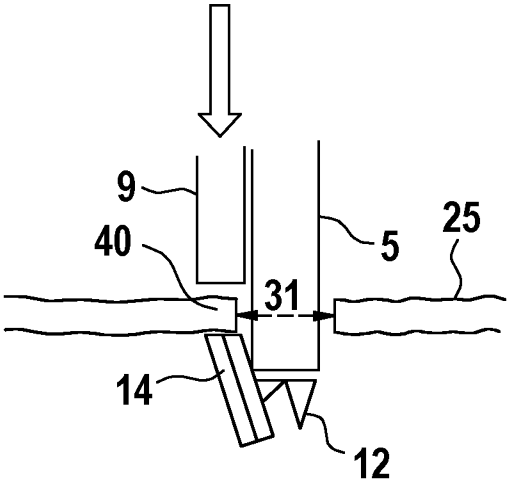
Figure 6D:
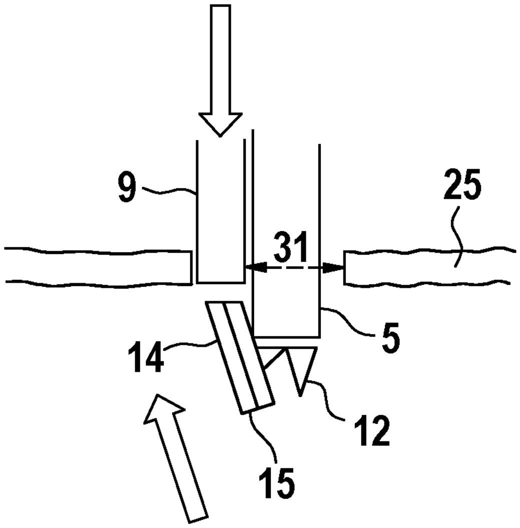
Figure 6E:
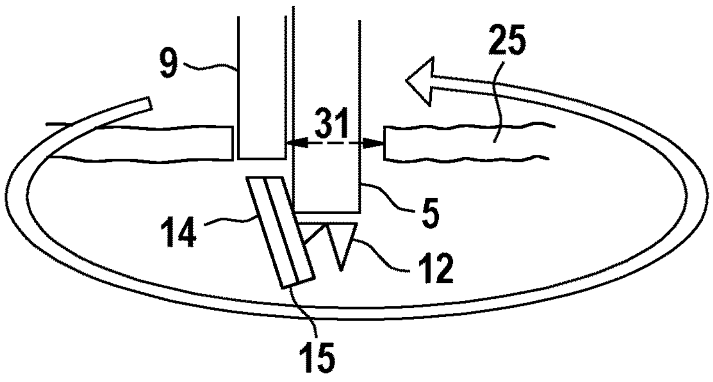
Figure 6F:
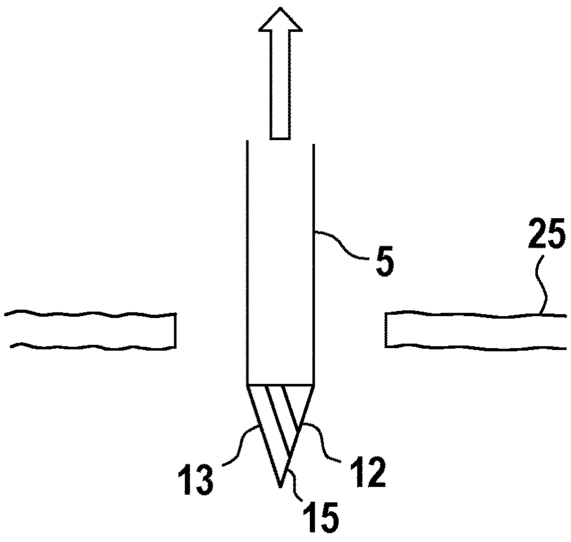
Figure 6G:
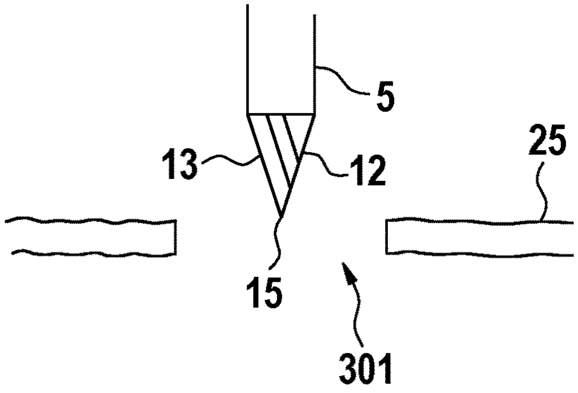

FIGS. 6*a* to 6*g* show an alternative embodiment of the insertable element 12 in the stowed configuration 13 and deployed configuration 14 cutting tissue with the counter element 9. FIG. 6*a* shows the insertable element 12 in the stowed configuration 13 with a lateral profile corresponding to the entry opening 31 in the tissue. FIG. 6*b* shows that the lateral profile of the insertable element 12 is increased by folding radially outward mechanically. However, also an inflatable and/or a rotatable insertion element 12 would also be conceivable. FIGS. 6*c* and 6*d* show the formation of an enclosed interface 40 of tissue between the counter element 9 on the proximal side of the tissue and the insertable element 12 in the deployed configuration 14 on the distal side of the tissue. The cut-out tissue can be clenched in the interface 40 and removed through the tube (not shown in FIG. 6*d*-6*g*). The insertable element 12 and counter element 9 can be rotatable around the entry opening 31. A section of the tissue wall 25 can be cut and the edges of the interface 40 can be fixated (e.g. sutured and/or stapled) by the fixation device 15. FIG. 6*e*-6*g* show that the insertable element 12 in the stowed configuration 13 can be removed consequently. It is not shown explicitly in the FIGS. 5*a*-5*g* and 6*a*-6*g* but the tissue wall 25 can comprise in fact the tissue wall of the first area of the stomach 201 and the second area of the bowel 202. After creation of anastomosis 301 the insertable element 12 in the stowed configuration 13 can be removed by retracting the operating element 5.

Figure 7A:
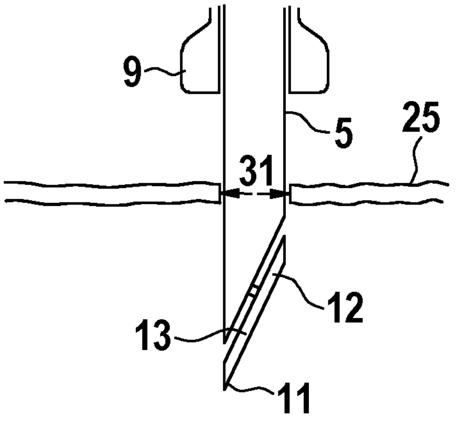
Figure 7B:
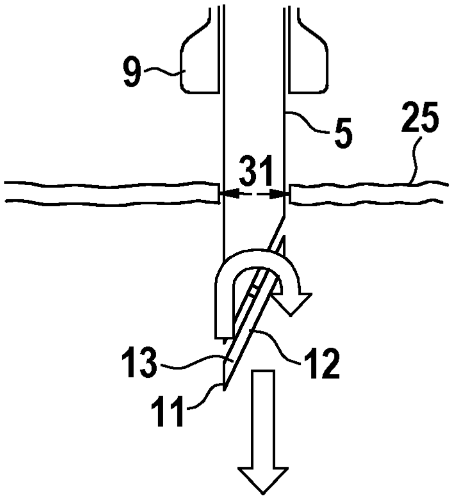
Figure 7C:
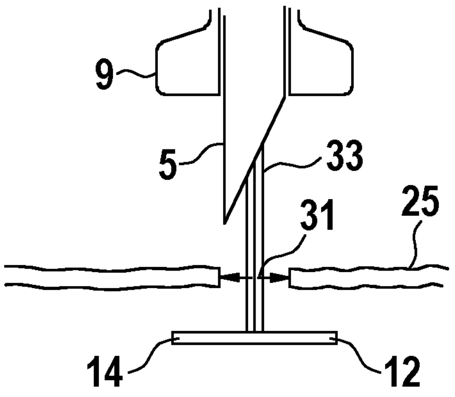
Figure 7D:
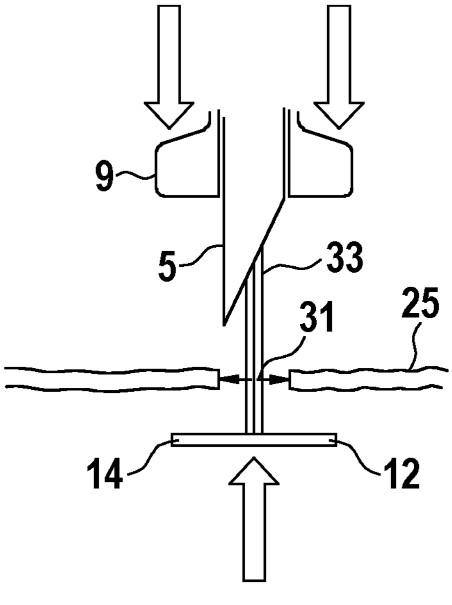
Figure 7E:
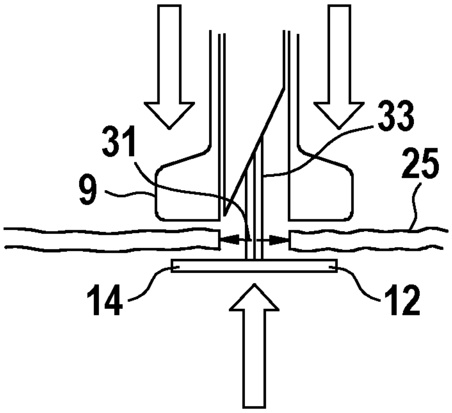
Figure 7F:
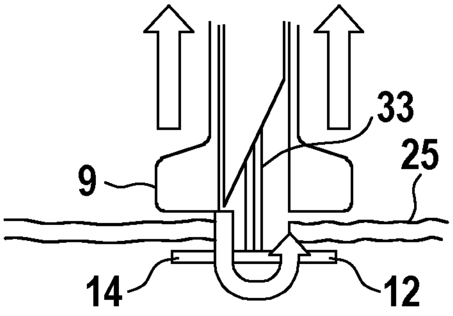
Figure 7G:
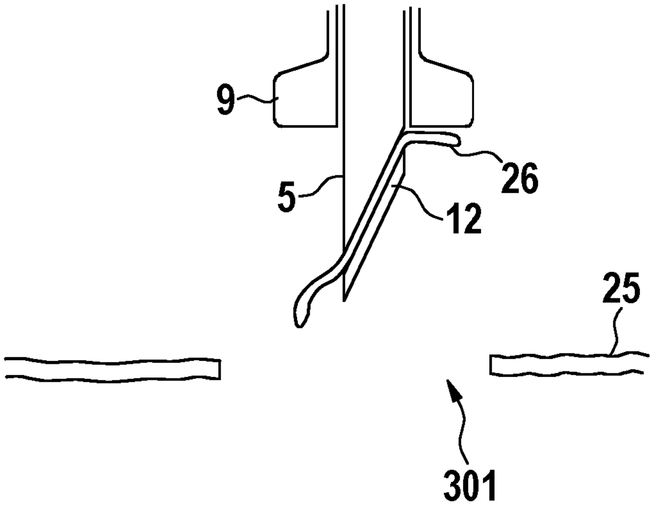

FIGS. 7*a* to 7*g* show an alternative embodiment of the apparatus with an insertable element 12 in the stowed configuration 13 and deployed configuration 14 cutting tissue with the counter element 9. FIG. 7*a*-7*g* are largely analogous to FIG. 5*a*-5*h* and/or FIG. 6*a*-6*g* and the same description applies respectively. As shown in FIG. 7*a* the counter element 9 can be arranged concentrically to the operating element 5. FIG. 7*b* shows that the distal region of the insertable element 12 in the stowed configuration 13 comprises a piercing element 11 which can be inserted in the entry opening 31. The operating element 5 comprises connection means 33 to the insertable element 12 which allow for a rotation of the insertable element 12 in the deployed configuration 14. In the deployed configuration 14 the lateral profile of the insertable element 12 is increased in relation to the stowed configuration 13. The insertable element 12 can rotate freely in order adapt to the surface conditions of a tissue surface but a rotation around a fixed angle would also be conceivable.

FIG. 7*c*-7*f* show that the connection means 33 can be moved relative to the counter element 9 in order to enclose the tissue wall 25 between the insertable element 12 in the deployed configuration 14 and the counter element 9.

The counter element 9 and the insertable element 12 are designed to enclose tissue concentrically around the entry opening 31. The cutting device can cut-out a section of the enclosed first and/or second area tissue walls 25 (not shown in the figures). The cut-out tissue 26 can be clenched between the insertable element 12 and the operating element 5 in order to be removed through the tube.

Figure 8A:
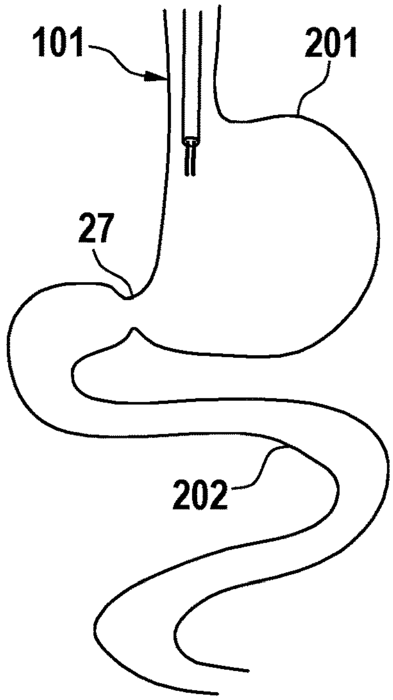
Figure 8B:
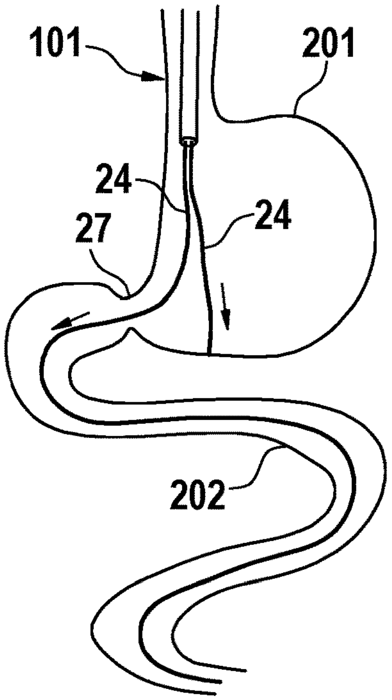
Figure 8C:
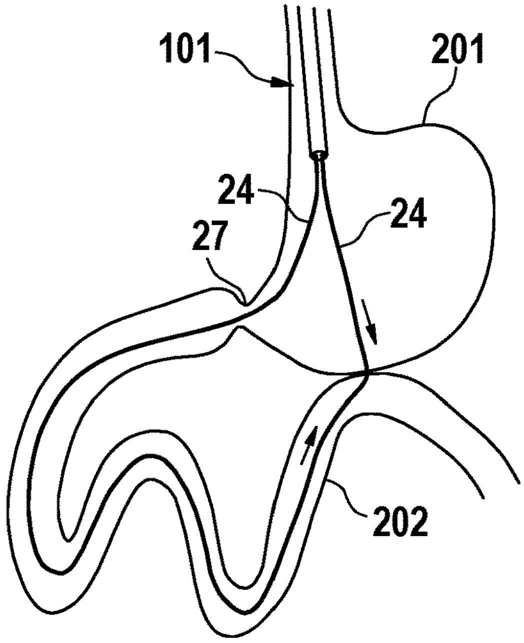
Figure 8D:
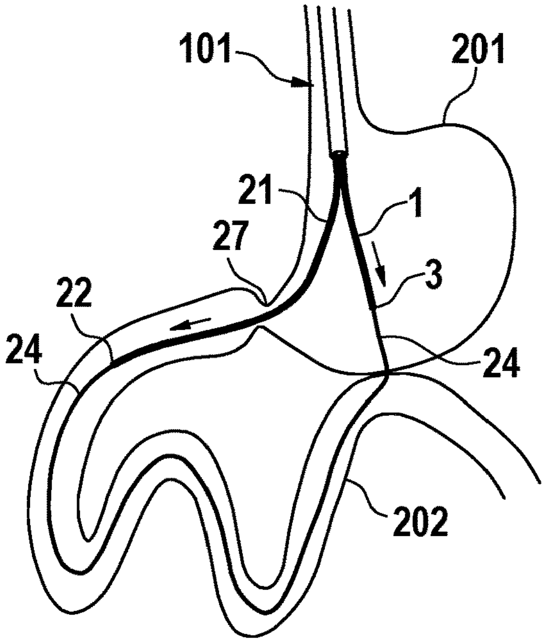
Figure 8E:
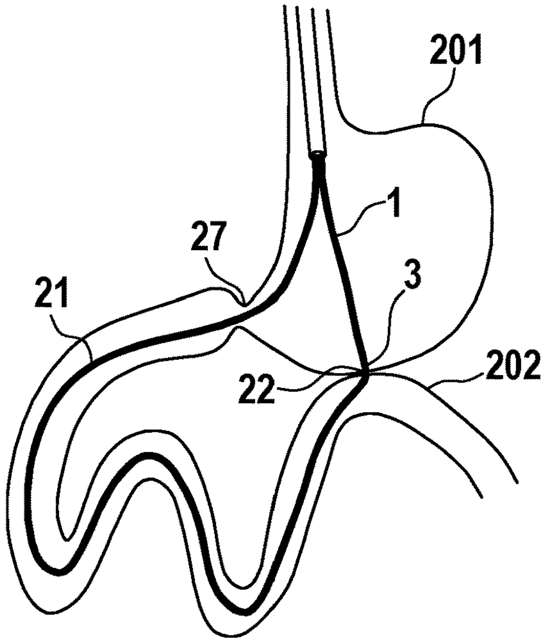

FIGS. 8*a*-8*g* show a surgical anastomosis 301 of the apparatus 101 using a guiding wire 24. The apparatus 101 comprises two guiding wires 24 which can be inserted into the stomach 201. FIG. 8*b* shows that one guiding wire 24 can be inserted at the first area in the stomach 201. The other guiding wire 24 can be inserted through the pylorus 27 and duodenum to the second area inside the bowel 202. FIG. 8*c* shows that distal ends of the two guiding wires 24 can be connected across the tissue wall of the stomach 201 and bowel 202. FIGS. 8*d* and 8*e* show that the tube 1 and the second tube 21 can be advanced along the guiding wire 24.

Figure 8F:
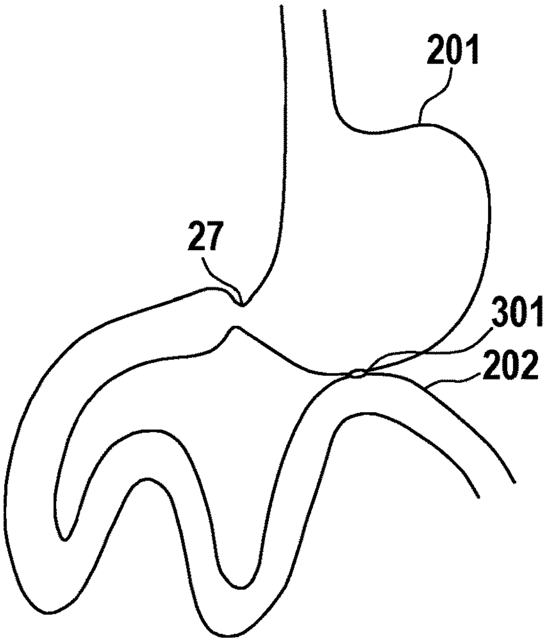

FIG. 8*e* further shows that the distal end 22 of the second tube and distal end 3 of the tube 1 can be connected across the tissue walls of the stomach 201 and bowel 202 across the first and second area. FIG. 8*f* shows that the apparatus 101 can be removed after successfully creating an anastomosis 301.

Figure 8G:
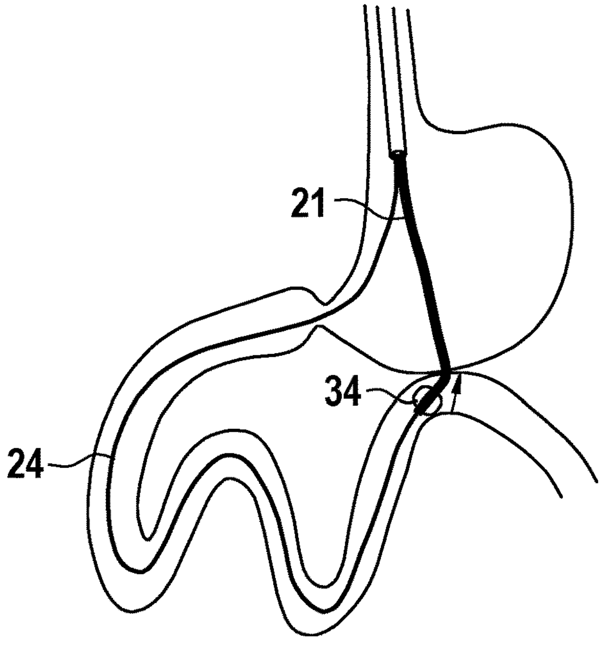

FIG. 8*g* shows that fusing means 20 which are illustrated in FIG. 9*a* and FIG. 9*b* can be advanced along the guiding wire 24. The fusing means 20 are designed to establish close contact of the first area and second area. For establishing close contact, the fusing means 20 can comprise a deployable balloon 34. However, fusing means 20 with deployable flanges 35 (shown in FIG. 9*a* and FIG. 9*b*) would also be conceivable. The fusing means 20 can be placed between the cut-out area in the first area and second area of by guiding the tube 1 or the second tube 21 along the guiding wire 24.

The fusing means 20 are designed to cause the fusion of tissue by applying a compressive force and heating.

FIG. 9*a* shows the fusing means 20 with closed flanges 35 and FIG. 9*b* shows the fusing means 20 with open flanges 35. In the embodiment in FIG. 9*a* and FIG. 9*b* the tissue can be clamped by flanges 35 and heated through radio-frequency heating. However, other means for heating could also be conceived. The distal end 38 of the fusing means 20 is shaped conical for easier insertion in the region of the first area and second area to create an anastomosis 301 by fusing the tissue edges. The lateral profile of the anastomosis 301 is determined by the lateral width 36 of the fusing means 20 in the region between the flanges 35. The anastomosis 301 using the fusing means 20 can establish permanent communication between the stomach 201 and the bowel 202. After the procedure the fusing means 20 can be retrieved and there is no need for a permanent implant, sutures and/or staples.

FIGS. 10 and 11, illustrate an optional technique to supplement an anastomosis, however formed (and not shown explicitly in FIG. 10). The technique involves application of at least one tissue-penetrating fixing 80 to reduce the natural volume of the stomach by creating one or more pleats 82 (or artificial folds) in the stomach wall. In the illustrated example, the fixing 80 is a staple, optionally having a U-shaped profile, with T-shaped limb ends. The fixing (s) may, for example, be placed by an endoscopic technique or a laparoscopic technique. Optionally, the fixing (s) may be placed using the same apparatus as that used for forming the anastomosis, or a different apparatus may be used.

The one or more pleats 82 may extend in a direction that is generally (i) from top to bottom of the stomach, and/or (ii) from the oesophagus to the pylorus. Such pleats 82 can form a generally sleeve shape cavity or passage in the stomach.

It will be appreciated that the foregoing description is merely a non-limiting description of illustrative examples of the invention, and does not limit the scope of protection. Protection is claimed for any novel feature and/or idea described herein and/or illustrated in the drawings, whether or not emphasis has been placed thereon.

The invention claimed is:

1. An apparatus for endoscopic anastomosis of the stomach and the bowel of a patient to allow food to bypass the duodenum, comprising:

a tube insertable into the stomach, the tube having a proximal end and a distal end;

surgical apparatus which is deployable at the distal end of the tube and is at least partially insertable through the tube; and at least one operating element connected or connectable to the surgical apparatus for operating the surgical apparatus from the proximal end;

wherein the surgical apparatus is configured for establishing anastomosis between a first area of the stomach and a second area of the bowel;

wherein the surgical apparatus comprises a cutting device for cutting tissue;

wherein the cutting device is convertible between (i) a stowed configuration for introduction to the first and/or second area, the stowed configuration having a first lateral profile about an axis of the tube; and (ii) a deployed configuration for operative cutting of tissue, the deployed configuration having a second lateral profile about an axis of the tube larger than the first lateral profile.

2. The apparatus according to claim 1, wherein the cutting device is rotatable in the direction along the circumference of the tube.

3. The apparatus according to claim 1, wherein the cutting device is mounted on a shaft, wherein the cutting device is configured for cutting a closed-loop shape aperture in tissue, the closed loop shape extending around an axis of the shaft.

4. The apparatus according to claim 1, wherein the cutting device, when deployed for cutting, has a cutting element and/or cutting surface facing towards the distal end of the tube.

5. The apparatus according to claim 1, wherein the cutting device, when deployed, is configured for cutting tissue in a cutting direction towards the distal end of the tube.

6. The apparatus according to claim 1, wherein the cutting device is configured for cutting tissue from a first side, and the apparatus further comprises a counter element deployable on an opposite second side of the tissue.

7. The apparatus according to claim 6, wherein the cutting device is positioned distally of the counter element, at least in the deployed configuration of the cutting device.

8. The apparatus according to claim 6, wherein the counter element is configured to (i) protect surrounding tissue on the second side from the cutting device, and/or (ii) provide a cutting board for the cutting device, and/or (iii) co-operate with the cutting device to capture cut-out tissue for removal through the tube.

9. The apparatus according to claim 6, wherein the counter element is convertible between (i) a stowed configuration for introduction to the first and/or second area, the stowed configuration having a first lateral profile about an axis of the tube; and (ii) a deployed configuration having a second lateral profile about an axis of the tube larger than the first lateral profile.

10. The apparatus according to claim 6, wherein the apparatus comprises at least one insertable element insertable through a tissue wall at the first and/or second area, the insertable element having a stowed configuration for introduction through the tissue wall, and being expandable to a deployed configuration for overlapping, at least partially, tissue of the tissue wall.

11. The apparatus according to claim 10, wherein the insertable element is movable relative to the tube up to 20 cm from a distal end of the tube.

12. The apparatus according to claim 10, wherein the distal region of the insertable element in the stowed configuration comprises a second cutting device for piercing and/or cutting tissue.

13. The apparatus according to claim 10, wherein at least two of: the insertable element in the deployed configuration; the counter element in the deployed configuration; or the cutting device, are adapted to form an interface to enclose tissue.

14. The apparatus according to claim 10, wherein the insertable element is foldable radially outward from the longitudinal axis of the tube from the stowed configuration into the deployed configuration.

15. The apparatus according to claim 1, wherein the cutting device comprises at least one selected from: a blade element, a piercing element, and an electrical or optical ablation element.

16. The apparatus according to claim 1, wherein the cutting device is movable during cutting, in a rotary direction following a curve and/or in an axial direction.

17. The apparatus according to claim 1, wherein the apparatus comprises an implantable stent comprising a non-return mechanism convertible between an open state and a closed state, wherein the closed state prevents passage of fluid and an open state enables crossing of fluid or a non-return valve enabling only one-directional passage of fluid.

18. The apparatus according to claim 1, wherein the apparatus comprises a pressure device for selectively applying a negative pressure to at least one area in the tube and/or a retaining element in an area at a distal end of the apparatus for retaining a distal end of the apparatus to tissue.

19. The apparatus according to claim 1, wherein, the apparatus comprises a fixation device, wherein the fixation device is designed to suture and/or staple the outer edges of the first area and the second area.

20. The apparatus according to claim 19, wherein the fixation device comprises fusing means, wherein the fusing means are designed to cause fusion of tissue of the first area of the stomach and the second area of the bowel, by applying a pressure and heating at least on the edges of the first area and the second area.

21. The apparatus according to claim 1, wherein the device comprises a second tube, wherein a distal end of the second tube is guidable from the stomach through the duodenum and connectable with the distal end of the tube across the stomach wall of the first area and the bowel wall of the second area.

22. The apparatus according to claim 21, wherein the apparatus comprises a guiding wire, wherein the tube and/or second tube can be guided along the guiding wire to enclose the first area and/or second area.

23. The apparatus according to claim 1, wherein the apparatus is configured to create the anastomosis by insertion of the apparatus into the body via a single orifice, the orifice being a natural body orifice.

24. An apparatus for endoscopic anastomosis of the stomach and the bowel of a patient to allow food to bypass the duodenum, comprising:

a tube insertable into the stomach, the tube having a proximal end and a distal end;

surgical apparatus which is deployable at the distal end of the tube and is at least partially insertable through the tube; and at least one operating element connected or connectable to the surgical apparatus for operating the surgical apparatus from the proximal end;

wherein the surgical apparatus is configured for establishing anastomosis between a first area of the stomach and a second area of the bowel;

wherein the surgical apparatus comprises a cutting device for cutting tissue; and wherein the cutting device is convertible between (i) a stowed configuration for introduction to the first and/or second area, the stowed configuration having a first lateral profile about an axis of the tube; and (ii) a deployed configuration for operative cutting of tissue, the deployed configuration having a second lateral profile about an axis of the tube larger than the first lateral profile; and wherein the second lateral profile has a predetermined size, and the cutting device is configured to cut tissue when in the deployed configuration.

* * * * *